United States Patent [19]

Skidmore et al.

[11] Patent Number: 4,992,474
[45] Date of Patent: Feb. 12, 1991

[54] PHENETHANOLAMINE DERIVATIVES

[75] Inventors: Ian F. Skidmore, Welwyn; Lawrence H. C. Lunts, Broxbourne; Harry Finch, Hitchin; Alan Naylor, Royston, all of England

[73] Assignee: Glaxo Group Ltd., London, England

[21] Appl. No.: 397,664

[22] Filed: Aug. 23, 1989

Related U.S. Application Data

[63] Continuation of Ser. No. 932,359, Nov. 19, 1986, which is a continuation of Ser. No. 601,444, Apr. 18, 1984.

[30] Foreign Application Priority Data

Apr. 18, 1983 [GB] United Kingdom ............... 8310477
Jun. 23, 1983 [GB] United Kingdom ............... 8317087
Nov. 4, 1983 [GB] United Kingdom ............... 8329568
Jan. 25, 1984 [GB] United Kingdom ............... 8401889

[51] Int. Cl.$^5$ ............... A61K 31/135; C07C 215/00
[52] U.S. Cl. ............... 514/653; 514/826; 564/353; 564/354
[58] Field of Search ............... 564/353, 354; 514/651

[56] References Cited

U.S. PATENT DOCUMENTS

| | | | |
|---|---|---|---|
| 3,644,353 | 2/1972 | Lunts et al. | 260/247.5 R |
| 3,879,442 | 4/1975 | Schwender et al. | 260/471 R |
| 4,021,485 | 5/1977 | Schromm et al. | 260/570.6 |
| 4,154,761 | 5/1979 | Collins et al. | 260/570.5 P |
| 4,160,036 | 7/1979 | Bradshaw et al. | 424/330 |
| 4,396,627 | 8/1983 | Ainsworth et al. | 424/309 |

OTHER PUBLICATIONS

D. T. Collin et al., "Saligenin Analogs of Sympathomimetic Catecholamines," *J. Med. Chem.*, 13, 674–680 (1980).

Primary Examiner—Robert V. Hines
Attorney, Agent, or Firm—Morgan & Finnegan

[57] ABSTRACT

Phenethanolamine derivatives are disclosed of formula

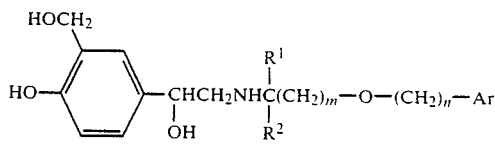

wherein
m is 2 to 8; n is 1 to 7 provided that m+n is 4 to 12;
Ar is phenyl or phenyl substituted by one or two halogen atoms, alkyl or alkoxy groups or by an alkylenedioxy group;
$R^1$ and $R^2$ are hydrogen or alkyl provided that the sum total of carbon atoms in $R^1$ and $R^2$ is not more than 4;

and the physiologically acceptable salts and solvates thereof.

The compounds have a selective stimulant action at $\beta_2$-adrenoreceptors and may be used inter alia in the treatment of diseases associated with reversible airways obstructions such as asthma and chronic bronchitis. The compounds may be formulated in conventional manner as pharmaceutical compositions with physiologically acceptable carriers or excipients.

The compounds may be prepared, for example by alkylation of an amine:

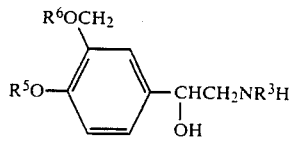

where $R^3$, $R^5$ and $R^6$ is hydrogen or a protecting group, followed by removal of any protecting group.

12 Claims, No Drawings

PHENETHANOLAMINE DERIVATIVES

This application is a continuation of U.S. Ser. No. 06/932,359, filed on Nov. 19, 1986, which is a continuation of U.S. Ser. No. 06/601,444 filed Apr. 18, 1984.

This invention relates to phenethanolamine compounds having a stimulant action at $\beta_2$-adrenoreceptors, to processes for their preparation, to pharmaceutical compositions containing them and to their use in medicine.

Certain phenethanolamine compounds are known to possess either stimulant or blocking actions at $\beta$-adrenoreceptors. For example, British Patent Specification No. 1200886 describes a group of such phenethanolamines of general structure:

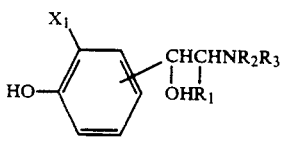

where, inter alia, $X_1$ is hydroxyalkyl, $R_1$ and $R_2$ is each a hydrogen atom, and $R_3$ is straight or branched $C_{1-6}$ alkyl, aralkyl or aryloxyalkyl. One compound from within this particular group has been developed for clinical use. This is salbutamol [($\alpha^1$-tert-butylaminomothyl)-4-hydroxy-m-xylene-$\alpha^1,\alpha^3$-diol; $X_1=CH_2OH$, $R_1=-H$; $R_2=-H$; $R_3=$t-butyl, above] which at the present time is widely prescribed for the treatment of conditions such as bronchial asthma and chronic bronchitis. The success of salbutamol devolves from its profile of action, in particular its potency, coupled with a selective stimulant action at $\beta_2$-adrenoreceptors.

All $\beta_2$-stimulants currently used in clinical practice suffer from the disadvantage that they have a relatively short duration of action when administered by inhalation. A $\beta_2$-stimulant with a relatively long duration of action would therefore offer a significant advance in the treatment of bronchial asthma and related disorders.

In a search for new $\beta$-stimulants with advantageous properties, we have now found a novel group of phenethanolamine derivatives, which differ structurally from the group of compounds described in British Patent Specification No. 1200886, and which in our tests have shown a potent selective stimulant action at $\beta_2$-adrenoreceptors, and, in addition, have an advantageous profile of action.

Thus, the present invention provides compounds of the general formula (I)

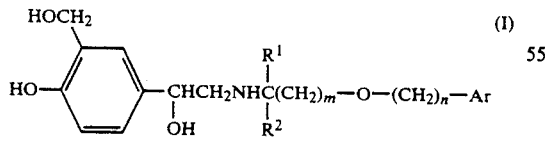

wherein
m is an integer from 2 to 8 and
n is an integer from 1 to 7 with the proviso that the sum total of m+n is 4 to 12;
Ar represents a phenyl group optionally substituted by one or two substituents selected from halogen atoms, $C_{1-3}$ alkyl or $C_{1-3}$ alkoxy groups, or by an alkylenedioxy group of formula $-O(CH_2)_pO-$ where p is 1 or 2; and $R^1$ and $R^2$ each represents a hydrogen atom or a $C_{1-3}$ alkyl group with the proviso that the sum total of carbon atoms in $R^1$ and $R^2$ is not more than 4;
and physiologically acceptable salts and solvates (e.g. hydrates) thereof.

It will be appreciated that the compounds of general formula (I) possess one or two asymmetric carbon atoms, namely the carbon atom of the

group and, when $R^1$ and $R^2$ are different groups, the carbon atom to which these group are attached.

The compounds according to the invention thus include all enantiomers, diastereoisomers and mixtures thereof, including racemates. Compounds in which the carbon atom in the

group is in the R configuration are preferred.

In the general formula (I), the chain $-(CH_2)_m-$ may be, for example, $-(CH_2)_3-$, $-(CH_2)_4-$, $-(CH_2)_5-$, $-(CH_2)_6-$ or $-(CH_2)_7-$, and the chain $-(CH_2)_n-$ may be, for example, $-(CH_2)_2-$, $-(CH_2)_3-$, $-(CH_2)_4-$, $-(CH_2)_5-$ or $-(CH_2)_6-$.

Preferably the sum total of the number of carbon atoms in the chains $-(CH_2)_m-$ and $-(CH_2)_n$ is 6 to 12 inclusive and may be, for example, 7, 8, 9 or 10. Compounds wherein the sum total of m+n is 7, 8 or 9 are particularly preferred.

Preferred compounds of general formula (I) are those wherein m is 3 and n is 6, or m is 4 and n is 3, 4 or 5, or m is 5 and n is 2, 3, 4 or 5, or m is 6 and n is 2 or 3.

$R^1$ and $R^2$, for example, may each be methyl, ethyl, propyl, or isopropyl groups except that if one of $R^1$ and $R^2$ is a propyl or isopropyl group, the other is a hydrogen atom or a methyl group. Thus, for example, $R^1$ may be a hydrogen atom or a methyl, ethyl or propyl group. $R^2$, for example, may be a hydrogen atom or a methyl group.

$R^1$ and $R^2$ are each preferably a hydrogen atom or a methyl group.

A preferred group of compounds is that wherein $R^1$ and $R^2$ are both hydrogen atoms. In another preferred group of compounds $R^1$ is a hydrogen atom and $R^2$ is a $C_{1-3}$ alkyl group, particularly a methyl group. In yet another preferred group of compounds $R^1$ and $R^2$ are both methyl groups.

The chain

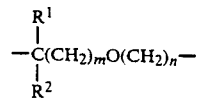

in general formula (I) may be, for example $-(CH_2)_4O(CH_2)_4-$, $(CH_2)_5O(CH_2)_2-$ $-(CH_2)_5O(CH_2)_3$, $-(CH_2)_5O(CH_2)_4-$,

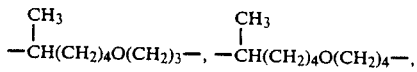

-continued

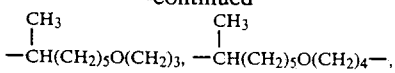

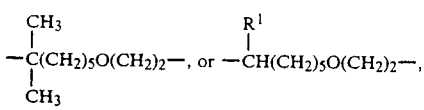

where R¹ is methyl, ethyl or propyl.

Examples of the optional substituents which may be present on the phenyl group represented by Ar include bromine, iodine or, in particular, chlorine or fluorine atoms, or methyl, ethyl, methoxy or ethoxy groups. In general, Ar is preferably an unsubstituted phenyl group. According to another preference, Ar is a phenyl group substituted by one substituent, particularly a fluorine or chlorine atom or a methoxy or methyl group.

Suitable physiologically acceptable salts of the compounds of general formula (I) include acid addition salts derived from inorganic and organic acids, such as hydrochlorides, hydrobromides, sulphates, phosphates, maleates, tartrates, citrates, benzoates, 4-methoxybenzoates, 2- or 4-hydroxybenzoates, 4-chlorobenzoates, p-toluenesulphonates, methanesulphonates, ascorbates, salicylates, acetates, fumarates, succinates, lactates, glutarates, gluconates, tricarballylates, hydroxynaphthalenecarboxylates e.g. 1-hydroxy- or 3-hydroxy-2-naphthalenecarboxylates, or oleates. The compounds may also form salts with suitable bases. Examples of such salts are alkali metal (e.g. sodium and potassium), and alkaline earth metal (e.g. calcium and magnesium) salts.

The compounds according to the invention have a selective stimulant action at $\beta_2$-adrenoreceptors, which furthermore is of a particularly advantageous profile. The stimulant action was demonstrated in the guinea-pig, where compounds were shown to cause relaxation of PGF2α-contracted isolated trachea. In another test, compounds of the invention were shown to afford protection against histamine-induced broncho-constriction when administered by inhalation or by an oral route in conscious guinea-pigs. In both tests, compounds according the invention have shown a particularly long duration of action. The selective action of compounds of the invention was demonstrated in the rat or guinea pig. Where compounds were shown to have little or no effect on isolated rat or guinea pig left atria ($\beta_1$-adrenoreceptor tissues) at concentrations where they cause relaxation of PGF2α-contracted isolated trachea. Compounds according to the invention have also been shown to inhibit the anaphylactic release of spasmagens and inflammagens from sensitised human tissues e.g. lung fragments.

The compounds according to the invention may be used in the treatment of diseases associated with reversible airways obstruction such as asthma and chronic bronchitis.

The compounds according to the invention may also be used for the treatment of premature labour, depression and congestive heart failure, and are also indicated as useful for the treatment of inflammatory and allergic skin diseases, psoriasis, proliferative skin diseases, glaucoma, and in the treatment of conditions in which there is an advantage in lowering gastric acidity, particularly in gastric and peptic ulceration.

A particularly important group of compounds by virtue of the advantageously long duration of action they have shown in our tests, has the formula (Ia):

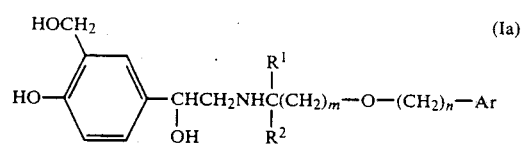

in which
R¹ and R² are as defined for general formula (I);
m is an integer from 3 to 6,
n is an integer from 2 to 6,
and Ar is phenyl or phenyl substituted by a methoxy or methyl group, or more preferably a fluorine or chlorine atom, and the physiologically acceptable salts and solvates thereof, in each instance the sum total of carbon atoms in the chains —$(CH_2)_m$— and —$(CH_2)_n$— being an integer from 7 to 10 inclusive, in particular 7, 8 or 9.

A preferred group of compounds of formula (Ia) is that wherein R¹ and R² is each a hydrogen atom.

In another preferred group of compounds of formula (Ia) R¹ is a hydrogen atom or a methyl group and R² is a methyl group.

In a further group of compounds of formula (Ia) R¹ and R² each is a hydrogen atom and Ar is phenyl or phenyl substituted by a methoxy group, or more preferably a fluorine or chlorine atom.

A particularly preferred group of compounds has the formula (Ia) in which R¹ and R² each is a hydrogen atom or a methyl group, m is 4 or 5, n is 2, 3 or 4, and Ar is phenyl or phenyl substituted by a chlorine or fluorine atom or a methoxy or methyl group and the physiologically acceptable salts and solvates thereof.

Particularly important compounds are:
4-hydroxy-α¹[[[6-(4-phenylbutoxy)hexyl]amino]methyl]-1,3-benzenedimethanol; and the physiologically acceptable salts thereof;
4-hydroxy-α¹[[[6-(3-phenylpropoxy)hexyl]amino]methyl]-1,3-benzenedimethanol; and the physiologically acceptable salts thereof;
4-hydroxy-α¹-[[[6-(2-phenylethoxy)hexyl]amino]methyl]-1,3-benzenedimethanol; and the physiologically acceptable salts thereof;
4-hydroxy-α¹-[[[5-(4-phenylbutoxy)pentyl]amino]methyl]-1,3-benzenedimethanol; and the physiologically acceptable salts thereof;
4-hydroxy-α¹-[[[1-methyl-6-(2-phenylethoxy)hexyl]amino]methyl]-1,3-benzenedimethanol; and the physiologically acceptable salts thereof;
4-hydroxy-α¹-[[[1-methyl-5-(3-phenylpropoxy)pentyl]amino]methyl]-1,3-benzenedimethanol; and the physiologically acceptable salts thereof;
4-hydroxy-α¹-[[[1-methyl-5-(4-phenylbutoxy)pentyl]amino]methyl]-1,3-benzenedimethanol; and the physiologically acceptable salts thereof;
4-hydroxy-α¹-[[[1-ethyl-6-(2-phenylethoxy)hexyl]amino]methyl]-1,3-benzenedimethanol; and the physiologically acceptable salts thereof;
α¹-[[[1,1-dimethyl-6-(2-phenylethoxy)hexyl]amino]methyl-4-hydroxy-1,3-benzenedimethanol; and the physiologically acceptable salts thereof;
α¹-[[[6-[2-(4-fluorophenyl)ethoxy]-1-methylhexyl]amino]methyl]-4-hydroxy-1,3-benzenedimethanol; and the physiologically acceptable salts thereof;

4-hydroxy-α$^1$-[[[6-[3-(4-methoxyphenyl)propoxy]-1-methylhexyl]amino]methyl]-1,3-benzenedimethanol; and the physiologically acceptable salts thereof;

4-hydroxy-α$^1$-[[[1-methyl-6-(4-phenylbutoxy)hexyl]amino]methyl]-1,3-benzenedimethanol; and the physiologically acceptable salts thereof;

4-hydroxy-α$^1$-[[[6-[2-(4-methylphenyl)ethoxy]hexyl]amino]methyl]-1,3-benzenedimethanol; and the physiologically acceptable salts thereof;

α$^1$-[[[6-[2-(3-chlorophenyl)ethoxy]hexyl]amino]methyl]-4-hydroxy-1,3-benzenedimethanol; and the physiologically acceptable salts thereof;

4-hydroxy-α$^1$-[[[6-[2-(4-methoxyphenyl)ethoxy]hexyl]amino]-methyl]-1,3-benzenedimethanol; and the physiologically acceptable salts thereof;

α$^1$-[[[6-[3-(4-fluorophenyl)propoxy]hexyl]amino]methyl]-4-hydroxy-1,3-benzenedimethanol; and the physiologically acceptable salts thereof.

The invention accordingly further provides compounds of formula (I) and their physiologically acceptable salts and solvates for use in the therapy or prophylaxis of diseases associated with reversible airways obstruction in human or animal subjects. The invention also provides compounds of formula (I) and their physiologically acceptable salts and solvates and compositions containing them in association with instructions for their use in the therapy or prophylaxis of diseases associated with reversible airways obstruction in human or animal subjects.

The compounds according to the invention may be formulated for administration in any convenient way. The invention therefore includes within its scope pharmaceutical compositions comprising at least one compound of formula (I) or a physiologically acceptable salt or solvate thereof formulated for use in human or veterinary medicine. Such compositions may be presented for use with physiologically acceptable carriers or excipients, optionally with supplementary medicinal agents.

The compounds may be formulated in a form suitable for administration by inhalation or insufflation, or for oral, buccal, parenteral, topical (including nasal) or rectal administration. Administration by inhalation or insufflation is preferred.

For administration by inhalation the compounds according to the invention are conveniently delivered in the form of an aerosol spray presentation from pressurised packs, with the use of a suitable propellant, such as dichlorodifluoromethane, trichlorofluoromethane, dichlorotetrafluoroethane, carbon dioxide or other suitable gas, or from a nebuliser. In the case of a pressurised aerosol the dosage unit may be determined by providing a valve to deliver a metered amount.

Alternatively, for administration by inhalation or insufflation, the compounds according to the invention may take the form of a dry powder composition, for example a powder mix of the compound and a suitable powder base such as lactose or starch. The powder composition may be presented in unit dosage form in, for example, capsules or cartridges of e.g. gelatin, or blister packs from which the powder may be administered with the aid of an inhaler or insufflator.

For oral administration, the pharmaceutical composition may take the form of, for example, tablets, capsules, powders, solutions, syrups or suspensions prepared by conventional means with acceptable excipients.

For buccal administration the composition may take the form of tablets, drops or lozenges formulated in conventional manner.

The compounds of the invention may be formulated for parenteral administration. Formulations for injections may be presented in unit dosage form in ampoules, or in multi-dose containers with an added preservative. The compositions may take such forms as suspensions, solutions or emulsions in oily or aqueous vehicles, and may contain formulatory agents such as suspending, stabilising and/or dispersing agents. Alternatively, the active ingredient may be in powder form for reconstitution with a suitable vehicle, e.g. sterile pyrogen-free water, before use.

For topical administration the pharmaceutical composition may take the form of ointments, lotions or creams formulated in a conventional manner, with for example an aqueous or oily base, generally with the addition of suitable thickening agents and/or solvents. For nasal application, the composition may take the form of a spray, formulated for example as an aqueous solution or suspension or as an aerosol with the use of a suitable propellant.

The compounds of the invention may also be formulated in rectal compositions such as suppositories or retention enemas, e.g. containing conventional suppository bases such as cocoa butter or other glyceride.

Where pharmaceutical compositions are described above for oral, buccal, rectal or topical administration, these may be presented in a conventional manner associated with controlled release forms.

A proposed daily dosage of active compound for the treatment of man is 0.0005 mg to 100 mg, which may be conveniently administered in one or two doses. The precise dose employed will of course depend on the age and condition of the patient and on the route of administration. Thus a suitable dose for administration by inhalation is 0.0005 mg to 10 mg, for oral administration is 0.02 mg to 100 mg, and for parenteral administration is 0.001 mg to 2 mg.

The compounds according to the invention may be prepared by a number of processes, as described in the following wherein m, n, Ar, R$^1$ and R$^2$ are as defined for general formula (I) unless otherwise specified. In the general processes (1) to (3) described below the final step in the reaction may be the removal of a protecting group. Suitable protecting groups and their removal are described in general process (4) below.

According to one general process (1), a compound of general formula (I) may be prepared by alkylation. Conventional alkylation procedures may be used.

Thus, for example, in one process (a), a compound of general formula (I) in which R$^1$ is a hydrogen atom may be prepared by alkylation of an amine of general formula (II):

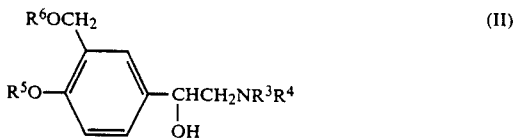

(II)

(wherein R$^3$, R$^5$ and R$^6$ each is a hydrogen atom or a protecting group and R$^4$ is a hydrogen atom) followed by removal of any protecting group where present.

The alkylating reaction (a) may be effected using an alkylating agent of general formula (III):

(wherein L represents a leaving group, for example a halogen atom such as chlorine, bromine or iodine, or a hydrocarbylsulphonyloxy group such as methanesulphonyloxy or p-toluenesulphonyloxy).

The alkylation is preferably effected in the presence of a suitable acid scavenger, for example, inorganic bases such as sodium or potassium carbonate, organic bases such as triethylamine, diisopropylethylamine or pyridine, or alkylene oxides such as ethylene oxide or propylene oxide. The reaction is conveniently effected in a solvent such as acetonitrile or an ether e.g. tetrahydrofuran or dioxan, a ketone e.g. butanone or methyl isobutyl ketone, a substituted amide e.g. dimethylformamide or a chlorinated hydrocarbon e.g. chloroform at a temperature between ambient and the reflux temperature of the solvent.

According to another example (b) of an alkylation process, a compound of general formula (I) in which $R^1$ represents a hydrogen atom may be prepared by alkylation of an amine of general formula (II), as previously defined except that $R^4$ is a hydrogen atom or a group convertible thereto under the reaction conditions, with a compound of general formula (IV):

in the presence of a reducing agent, followed when necessary by removal of any protecting groups.

Examples of suitable groups represented by $R^4$ which are convertible into a hydrogen atom are arylmethyl groups such as benzyl, α-methyl benzyl and benzhydryl.

Suitable reducing agents include hydrogen in the presence of a metal catalyst such as platinum, platinum oxide, palladium, Raney nickel or rhodium, on a support, such as charcoal, using an alcohol, e.g. ethanol or an ester e.g. ethyl acetate or an ether e.g. tetrahydrofuran, or water, as reaction solvent, or a mixture of solvents, e.g. a mixture of two or more of those just described, at normal or elevated temperature and pressure, for example from 20° to 100° C. and from 1 to 10 atmospheres.

Alternatively when one or both of $R^3$ and $R^4$ are hydrogen atoms, the reducing agent may be a hydride such as diborane or a metal hydride such as sodium borohydride, sodium cyanoborohydride or lithium aluminium hydride. Suitable solvents for the reaction with these reducing agents will depend on the particular hydride used, but will include alcohols such as methanol or ethanol, or ethers such as diethyl ether or tert-butyl methyl ether, or tetrahydrofuran.

When a compound of formula (II) wherein $R^3$ and $R^4$ are both hydrogen atoms is used, the intermediate imine of formula (V) may be formed:

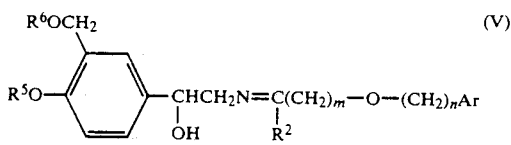

(wherein $R^6$ and $R^5$ are as defined for formula (II)).

Reduction of the imine using the conditions described above, followed, where necessary, by removal of any protecting groups, gives a compound of general formula (I).

Where it is desired to use a protected intermediate of general formula (II) it is particularly convenient to use hydrogen and a metal catalyst as described above with protecting groups $R^3$, $R^5$ and $R^6$ which are capable of being converted to a hydrogen atom under these reducing conditions, thus avoiding the need for a separate deprotection step. Suitable protecting groups of this type include arylmethyl groups such as benzyl, benzhydryl and α-methylbenzyl.

In a second general process (2), a compound of general formula (I) may be prepared by reduction. Thus, for example, a compound of general formula (I) may be prepared by reducing an intermediate of general formula (VI):

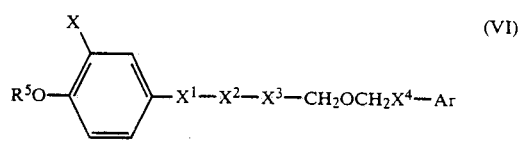

(wherein $R^5$ is as defined for general formula (II) and at least one of X, $X^1$, $X^2$, $X^3$ and $X^4$ represents a reducible group and the other(s) take the appropriate meaning as follows, which is X is $CH_2OR^6$, $X^1$ is —CH(OH)—, $X^2$ is —$CH_2NR^3$, $X^3$ is —$CR^1R^2(CH_2)_{m-1}$— and $X^4$ is —$(CH_2)_{n-1}$—) followed where necessary by removal of any protecting groups.

Suitable reducible groups include those wherein X is a group —$CO_2R^7$ (wherein $R^7$ represents a hydrogen atom, or an alkyl, aryl or aralkyl group) or —CHO, $X^1$ is a group —C=O, $X^2$ is a group —$CH_2NY$— (wherein Y represents a group convertible to hydrogen by catalytic hydrogenation, for example an arylmethyl group such as benzyl, benzhydryl or α-methylbenzyl), or an imine (—CH=N—) group or a group —CONH—, and $X^3$ is a group —$CO(CH_2)_{m-1}$—, or a group —$CR^1R^2X^5$— where $X^5$ is $C_{2-7}$alkenylene or $C_{2-7}$alkynylene, or $X^2$—$X^3$— is a group —$CH_2N$=$CR^2(CH_2)_{m-1}$, and $X^4$ is $C_{2-6}$alkenylene or $C_{2-6}$alkynylene. In one convenient aspect of the reduction process, the group $R^5$ may be a group convertible to hydrogen under the reducing conditions employed and may be for example an arylmethyl group such as benzyl, benzhydryl or α-methylbenzyl.

The reduction may be effected using reducing agents conveniently employed for the reduction of carboxylic acids, aldehydes, esters, ketones, imines, amides, ethylenes, acetylenes and protected amines. Thus, for example, when X in general formula (VI) represents a group —$CO_2R^7$ or —CHO this may be reduced to a group —$CH_2OH$ using a hydride such as diborane or a complex metal hydride such as lithium aluminium hydride, sodium bis(2-methoxyethoxy)aluminium hydride, sodium borohydride, diisobutylaluminium hydride or lithium triethylborohydride in a solvent such as an ether, e.g. tetrahydrofuran or diethyl ether, or a halogenated hydrocarbon e.g. dichloromethane at a temperature from 0° C. to the reflux.

When $X^1$ in general formula (VI) represents a —C=O group this may be reduced to a —CH(OH)— group using hydrogen in the presence of a metal catalyst as previously described for process (1) part (b).

Alternatively, the reducing agent may be, for example, a hydride such as diborane or a metal hydride such as lithium aluminium hydride, sodium bis(2-methoxyethoxy) aluminium hydride, sodium borohydride or aluminium hydride. The reaction may be effected in a solvent, where appropriate an alcohol e.g. methanol or ethanol, or an ether such as tetrahydrofuran, or a halogenated hydrocarbon such as dichloromethane.

When $X^2$ in general formula (VI) represents a $CH_2NY$ group or the group $-CH=N-$, or $-X^2-X^3$ represents $-CH_2N=CR^2(CH_2)_{m-1}$ this may be reduced to a $-CH_2NH-$ or $-CH_2NHCHR^2(CH_2)_{m-1}$ group using hydrogen in the presence of a metal catalyst as previously described for process (1) part (b). Alternatively, when $X^2$ or $-X^2-X^3$ is the group $-CH=N-$ or $-CH_2N=CR^2(CH_2)_{m-1}$ this may be reduced to a $-CH_2NH-$ or $CH_2NHCHR_2(CH_2)_{m-1}$ group using a reducing agent and conditions as just described for the reduction of $X^1$ when this represents a $-C=O$ group.

When $X^2$ or $X^3$ in general formula (VI) represents a $-CONH-$ or $-CO(CH_2)_{m-1}-$ group this may be reduced to a group $-CH_2NH-$ or $-CH_2(CH_2)_{m-1}-$ using a hydride such as diborane or a complex metal hydride such as lithium aluminium hydride or sodium bis(2-methoxyethoxy)aluminium hydride in a solvent such as an ether, e.g.-tetrahydrofuran or diethyl ether.

When $X^3$ in general formula (VI) represents a group $-CR^1R^2X^5-$ this may be reduced to a group $-CR^1R^2(CH_2)_{m-1}-$ using hydrogen in the presence of a catalyst such as platinum or palladium on a support such as charcoal in a solvent such as an alcohol, e.g. ethanol or methanol, or an ester, e.g. ethyl acetate, or an ether, e.g. tetrahydrofuran, at normal or elevated temperature and pressure.

When $X^4$ is $C_{2-6}$alkenylene or $C_{2-6}$alkynylene this may be reduced to $-(CH_2)_{n-1}-$ using hydrogen and a catalyst as just described. In this aspect of the reduction process, suitable starting materials of formula (VI) include those in which $CR^1R^2X^5$ and/or $X^4$ each contains one $-C=C-$ or $-C\equiv C-$ linkage. Where both contain unsaturated linkages, these may be the same or different.

Particular examples of the reduction process are those in which a compound of general formula (I) in which $-(CH_2)_m-$ represents $-(CH_2)_5-$ is prepared from a corresponding compound in which $-(CH_2)_m-$ represents $-CH=CH(CH_2)_3-$, $-C\equiv C(CH_2)_3-$, $-(CH_2)_2CH=CHCH_2-$ or $-(CH_2)_2C\equiv CCH_2-$. In further examples, a compound of general formula (I) in which $-(CH_2)_n-$ represents $-(CH_2)_4-$ or $-(CH_2)_3-$ may be prepared by reduction of a corresponding compound of general formula (I) in which $-(CH_2)_n-$ represents $-CH_2CH=CH-CH_2$, $-CH_2C\equiv CCH_2$, $-CH_2CH_2CH=CH-$, $-CH_2CH_2C\equiv C-$, $-CH_2CH=CH$ or $-CH_2C\equiv C-$.

In the reduction processes just described the groups X and $R^5$ in a compound of formula (VI) may together conveniently represent a group

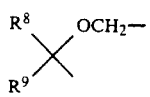

(where $R^8$ and $R^9$, which may be the same or different, each represents a hydrogen atom or an alkyl or aryl group. After the reduction is complete, cleavage of this group using e.g. a dilute acid in a solvent such as water at normal temperature yields a compound of formula (I).

According to a further general process (3), a compound of general formula (I) may be obtained by reaction of a compound of general formula (VII):

(wherein Z represents a group

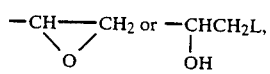

and L, $R^5$ and $R^6$ are as previously defined, with an amine of general formula (VIII):

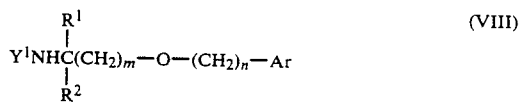

(wherein $Y^1$ is a hydrogen atom or a group convertible thereto by catalytic hydrogenation) followed by removal of any protecting groups where present, as described hereinafter.

Suitable $Y^1$ groups convertible into a hydrogen atom include arylmethyl groups such as benzyl, benzhydryl or α-methylbenzyl.

The reaction may be effected in the presence of a suitable solvent for example an alcohol, such as ethanol, a halogenated hydrocarbon e.g. chloroform, a substituted amide e.g. dimethylformamide or an ether such as tetrahydrofuran or dioxan at a temperature from ambient to the reflux, optionally in the presence of a base such as an inorganic amine e.g. diisopropylethylamine or an inorganic base such as sodium carbonate.

The intermediate amines of general formula (VIII) and their acid addition salts are novel compounds and form a further aspect of the invention. A particularly preferred group of amines of general formula (VIII) are those in which the total number of carbon atoms in the groups represented by

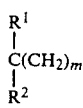

and $(CH_2)_n$ is from 7 to 13 inclusive.

In another general process (4), a compound of general formula (I) may be obtained by deprotection of a protected intermediate of general formula (IX):

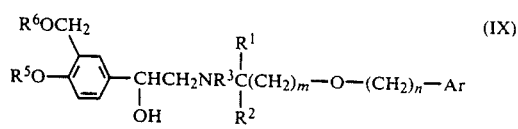

(wherein $R^3$, $R^5$ and $R^6$ are as previously defined except that at least one of $R^3$, $R^5$ and $R^6$ is a protecting group).

The protecting group may be any conventional protecting group, for example as described in "Protective Groups in Organic Chemistry", Ed. J.F.W. McOmie (Plenum Press, 1973). Examples of suitable hydroxyl protecting groups represented by $R^5$ and $R^6$ are aralkyl groups such as benzyl, diphenylmethyl or triphenylmethyl, and tetrahydropyranyl. Examples of suitable amino protecting groups represented by $R^3$ are aralkyl groups such as benzyl, α-methylbenzyl, diphenylmethyl or triphenylmethyl and acyl groups such as trichloroacetyl or trifluoroacetyl.

The deprotection to yield a compound of general formula (I) may be effected using conventional techniques. Thus, for example, when $R^5$, $R^6$ and/or $R^3$ is an aralkyl group this may be cleaved by hydrogenolysis in the presence of a metal catalyst (e.g. palladium on charcoal). When $R^5$ and/or $R^6$ is tetrahydropyranyl this may be cleaved by hydrolysis under acidic conditions. Acyl groups represented by $R^3$ may be removed by hydrolysis, for example with a base such as sodium hydroxide, or a group such as trichloroacetyl, or trifluoroacetyl may be removed by reduction with, for example, zinc and acetic acid.

In a particular embodiment of the deprotection process (4), $R^5$ and $R^6$ may together represent a protecting group as in a compound of general formula (X):

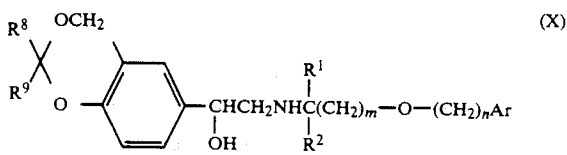

(wherein $R^8$ and $R^9$ are as previously defined).

A compound of general formula (X) may be obtained by treatment of a compound of formula (X) with a dilute acid, for example hydrochloric acid in a solvent such as water or an alcohol such as ethanol at normal or elevated temperature.

In the general processes (1) to (4) described above, the compound of formula (I) obtained may be in the form of a salt, conveniently in the form of a physiologically acceptable salt. Where desired such salts may be converted to the corresponding free base using conventional methods.

Physiologically acceptable salts of the compounds of general formula (I) may be prepared by reacting a compound of general formula (I) with an appropriate acid or base in the presence of a suitable solvent such as acetonitrile, acetone, chloroform, ethyl acetate or an alcohol e.g. methanol, ethanol or iso-propanol.

Physiologically acceptable salts may also be prepared from other salts, including other physiologically acceptable salts, of the compounds of general formula (I), using conventional methods.

When a specific enantiomer of a compound of general formula (I) possessing one asymmetric carbon atom is required, this may be obtained by resolution of a mixture of enantiomers of a corresponding compound of general formula (I) using conventional methods.

Thus, in one example an appropriate optically active acid may be used to form salts with a mixture of enantiomers of a compound of general formula (I). The resulting mixture of isomeric salts may be separated, for example by fractional crystallisation, into the diastereoisomeric salts from which the required enantiomer of a compound of general formula (I) may be isolated by conversion into the required free base.

Alternatively, enantiomers of a compound of general formula (I) possessing one asymmetric carbon atom may be synthesised from the appropriate optically active intermediates using any of the general processes described herein.

When a compound of formula (I) contains two asymmetric carbon atoms, specific diastereoisomers or enantiomers thereof may be obtained from an appropriate asymmetric starting material or by separation of an appropriate mixture of isomers using techniques just described.

Suitable methods for preparing the intermediate compounds used in the above general processes are described below. In the following discussion, Ar, m, n, $R^1$, $R^2$, $R^3$, $R^4$, Y and $Y^1$, Z, X, $X^1$, $X^2$, $X^3$ and L are as defined above except where otherwise indicated. "Hal" represents a halogen atom. Where an intermediate with protected hydroxyl and/or amino groups is desired, this may be obtained using conventional protection methods, for example those described by McOmie (see process (4) above).

The intermediate compounds of general formula (III) may be prepared by reaction of an alcohol of general formula (XI):

with a disubstituted alkane of general formula (XII):

(wherein $L^1$ is as previously defined for L, and L and $L^1$ may be the same or different), optionally in a solvent such as tetrahydrofuran or dimethylformamide at a temperature up to the boiling point. The reaction is effected by first generating the anion of the alcohol of general formula (XI) by adding for example sodium, sodium hydride or a strong base such as sodium hydroxide and a phase transfer catalyst such as tetrabutylammonium sulphate. Optionally a solvent such as dichloromethane or tetrahydrofuran may be added. The reaction can be carried out at ambient or elevated temperatures.

The compounds of general formulae (XI) and (XII) are either known compounds or they may be made by methods analogous to those used for the preparation of the known compounds.

Intermediate aldehydes of general formula (IV) (in which $R^2$ represents a hydrogen atom) may be prepared by oxidation of an alcohol of general formula (XIII):

with an oxidising agent such as pyridinium chlorochromate in a solvent such as a halogenated hydrocarbon, e.g. dichloromethane. The alcohols of formula (XIII) may be prepared from the compounds of formula (III), for example by reaction with sodium acetate, followed by hydrolysis of the product with for example sodium hydroxide.

Intermediate ketones of formula (IV) (in which $R^2$ represents an alkyl group), may be prepared by reaction of a Grignard complex of a halide of formula (XIV):

with an acyl halide $R^2COCl$ or anhydride $(R^2CO)_2O$ in a solvent such as an ether, for example diethyl ether or tetrahydrofuran. The halides of formula (XIV) may be prepared by alkylation of an alcohol of formula (XI) with a disubstituted alkane of formula $L(CH_2)_mHal$ as described above for the preparation of compounds of formula (III). Compounds $L(CH_2)_mHal$ are either known compounds or they may be made by methods analogous to those used for preparation of the known compounds.

Intermediate compounds of general formula (VI) for use in general process (2) may be prepared by a number of processes.

Thus for example intermediates of general formula (VI) in which $X^1$ is a group $-C=O$ may be prepared from a haloketone of formula (XV):

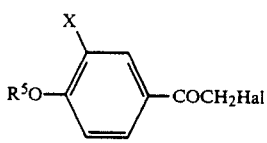

(XV)

by reaction with an amine of general formula (VIII). The reaction may be effected in a cold or hot solvent, for example tetrahydrofuran, tert-butyl methyl ether, dioxan, chloroform, dimethylformamide, acetonitrile or a ketone such as butanone or methylisobutylketone, or an ester, for example ethyl acetate preferably in the presence of a base such as diisopropylethylamine, sodium carbonate or other acid scavenger such as propylene oxide. When $-(CH_2)_m$ and/or $-(CH_2)_n-$ in the amine of formula (VIII) contains an unsaturated linkage, an intermediate of formula (VI) in which $X^3$ is $-CR^1R^2X^5-$ and/or $X^4$ is $C_{2-6}$alkenylene or $C_{2-6}$alkynylene may be obtained in this process.

Intermediates of general formula (VI) in which $X^1$ is a group $-C=O$ may be reduced to the corresponding intermediate in which $X^1$ is a group $-CH(OH)-$ using for example a metal hydride such as sodium borohydride in a solvent e.g. ethanol.

Iminoketones of general formula (VI) i.e. in which $X^2$ is a group $-CH=N-$ may be obtained from a phenylglyoxal derivative of formula (XVI):

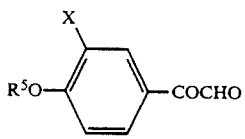

(XVI)

by reaction with an amine of formula (VIII) in which $Y^1$ represents a hydrogen atom, in a solvent such as benzene, tetrahydrofuran or an alcohol e.g. ethanol at temperatures up to the reflux. The phenylglyoxal derivatives of formula (XVI) may be obtained from a haloketone of formula (XV) by the action of a dialkylsulphoxide such as dimethylsulphoxide.

When X and $R^5$ in the glyoxal of formula (XVI) together represent a group

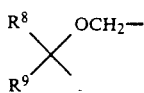

the iminoketone of formula (VI) so formed using this process subsequently may be reduced using a metal hydride such as sodium borohydride in a solvent such as ethanol to yield a compound of formula (X).

Intermediates of general formula (VI) in which $X^3$ is a group $-CO(CH_2)_m-$ may be prepared by acylation of an amine of formula (XVII):

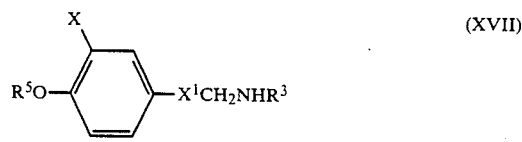

(XVII)

using an ester or an activated derivative of an acid of formula (XVIII):

$Ar(CH_2)_nO(CH_2)_mCO_2H$ (XVIII)

Suitable activated derivatives include the acid chloride, an anhydride or imidazolide. The reaction may be optionally carried out in a solvent such as tetrahydrofuran, benzene or chloroform, optionally in the presence of a base such as pyridine or triethylamine. The acids (XVIII) may be used directly if a coupling agent such as dicyclohexylcarbodiimide is added.

Acids of formula (XVIII) may be obtained by treatment of an alcohol of general formula (XIII) with a suitable oxidising agent, for example pyridinium dichromate in a solvent such as dimethylformamide.

Intermediates of formula (VI) in which $-X^2-X^3-$ represents $-CH_2N=CR^2(CH_2)_{m-1}$ may be obtained by reaction of an amine of formula (XVII) in which $R^3$ is a hydrogen atom with a compound of formula (IV) preferably in a solvent such as acetonitrile.

Intermediates of formula (VI) in which $X^2$ is $-CONH-$ may be prepared by reaction of an amine of formula (VIII) with an acid of formula (XIX)

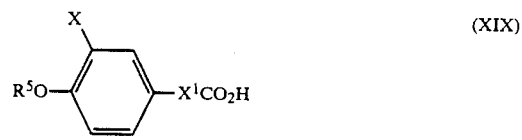

(XIX)

in the presence of a coupling agent such as dicyclohexylcarbodiimide.

Compounds of formula (VII) in which X represents a group

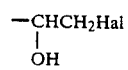

may be prepared from a haloketone of formula (XX):

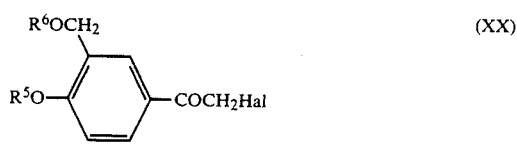

(XX)

by reduction using for example a metal hydride such as sodium borohydride in a solvent such as ethanol.

The halogen atom may be displaced to yield other compounds of general formula (VII) in which Z is a group

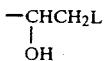

where L is a leaving group other than a halogen atom.
Compounds of formula (VII) wherein Z represents

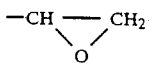

may be prepared from the corresponding compound in which Z is

by treatment with a base, for example an amine, which may be for example a compound of general formula (VIII), or an inorganic base such as sodium hydroxide in a solvent such as ethanol.

The amines of general formula (VIII) in which $Y^1$ is a group convertible to hydrogen and $R^1$ and $R^2$ are both hydrogen atoms may be prepared by reaction of a compound of general formula (III) in which $R^2$ is a hydrogen atom with an amine $YNH_2$. The reaction may be effected in the absence or presence of a solvent such as a ketone e.g. butanone or methyl isobutyl ketone, an ether e.g. tetrahydrofuran or a substituted amide e.g. dimethylformamide, optionally in the presence of a base such as sodium carbonate or an organic amine e.g. triethylamine or N,N-diisopropylethylamine at temperatures between 0° C. and the reflux. Where desired, subsequent reaction with hydrogen in the presence of a metal catalyst such as platinum in a solvent such as an alcohol e.g. ethanol yields a compound of formula (VIII) where $Y^1$ is a hydrogen atom.

Alternatively, amines of formula (VIII) in which $R^1$ is a hydrogen atom may be prepared by reductive alkylation of an amine $Y^1NH_2$, in which $Y^1$ is a group convertible into hydrogen with a compound of formula (IV), if necessary followed by conversion of the $Y^1$ group to a hydrogen atom as just described.

The reaction may be effected by hydrogen in the absence or presence of a solvent such as an alcohol, e.g. ethanol with a metal catalyst such as platinum or palladium, or by use of a complex metal hydride such as sodium borohydride or sodium cyanoborohydride in an alcohol, for example, ethanol.

A process to afford amines of formula (VIII) in which $R^1$ and $R^2$ can both be alkyl groups uses an acid of formula (XXI):

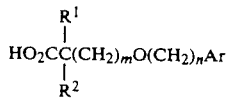

The acid is converted via its chloride and azide by a Curtius reaction into the amine of formula (VIII) in which $Y^1$ is a hydrogen atom. The reaction involves thermal rearrangement of the azide into an isocyanate, which is hydrolysed by treatment with an inorganic base, for example aqueous sodium hydroxide optionally in a solvent such as ethanol.

The acids of formula (XXI) can be prepared by alkylation of the acid (XXII):

via its dilithio derivative with an alkylating agent of formula (XIV) in a solvent such as an ether, for example tetrahydrofuran at low temperature such as 0° C. to ambient.

The compounds of formulae (II), (IV), (XVII), (XIX), (XX), (XXI) and (XXII) are either known compounds or may be obtained by analogous methods to those used for the preparation of the known compounds.

The following examples illustrate the invention.

Temperatures are in ° C. Thin layer chromatography (T.l.c.) was carried out over $SiO_2$ and 'dried' refers to drying using magnesium sulphate, except where otherwise stated.

The following abbreviations are used: DMF—dimethylformamide; THF—tetrahydrofuran; EA—ethyl acetate; ER—diethyl ether; CX—cyclohexane; HX—hexane; BR—brine; flash column chromatography [FCS]—on silica [FCTS]—on triethylamine-deactivated silica; T.l.c.EN—t.l.c. over triethylamine-deactivated $SiO_2$.

Eluants used for chromatography and t.l.c. are:
[A]-CX-ER(19:1); [B]-CX-ER(9:1); [C]-ER-CX-triethylamine (60:40:1); [D]-CX-ER(1:4); [E]-CX-EA(19:1); [F]-CX-ER(4:1); [G]-ER; [H]-EA; [I]-EA-methanol-triethylamine(9:1:0.1); [J]-CX-ER(7:3); [K]-CX-EA(9:1); [L]-CX-ER (3:1); [M]-EA-$CH_3OH$-$NH_3$(9:1:0.1); [N]-EA-$CH_3OH$(9:1); [O]-CX-ER(1:1).

INTERMEDIATE 1 is $\alpha^1$-(aminomethyl)-4-hydroxy-1,3-benzenedimethanol.

INTERMEDIATE 2

[2-[(6-Bromohexyl)oxy]ethyl]benzene

A mixture of phenethyl alcohol (20 g), 1,6-dibromohexane (195 g) and tetrabutylammonium bisulphate (3.0 g) in 50% w/v NaOH solution (100 ml) was heated at 65°-70° for 4 h. The cooled reaction mixture was poured into $H_2O$ (400 ml) and extracted with CX (2×300 ml). The dried extracts were evaporated in vacuo to give a yellow liquid which was purified by distillation under reduced pressure to give the title compound as a colourless liquid (26 g) b.p. 110°/0.1 mm. T.l.c. (EA) Rf 0.62.

INTERMEDIATE 3

[4-[(6-Bromohexyl)oxy]butyl]benzene

NaH (46% dispersion in oil; 6.5 g) was added portionwise to a solution of 4-phenyl-1-butanol (15.0 g) and 1,6-dibromohexane (48.8 g) in THF (200 ml) under nitrogen. The resulting suspension was refluxed for 27 h and treated with $H_2O$ (80 ml). The mixture was extracted with ER (2×200 ml) and the dried extract was evaporated to leave an orange oil. The oil was purified on a column of silica (800 ml) [A] to give a yellow oil which on distillation gave the title compound as a colourless oil (15.0 g) b.p. 90°-95°/0.1 mm Hg.

INTERMEDIATE 4 is $\alpha^1$-[[bis(phenylmethyl)amino]methyl]-4-hydroxy-1,3-benzenedimethanol.

INTERMEDIATE 5

6-(4-Phenylbutoxy)hexan-1-ol

A mixture of Intermediate 3 (10 g) sodium acetate trihydrate (34.8 g), $H_2O$ (25 ml) and trioctylpropyl $NH_4Cl$ (2 g) was stirred vigorously on a steam bath for 2.5 h. 2M NaOH (50 ml) and ethanol (50 ml) were added to the cooled mixture which was then stirred at RT for 30 min. The mixture was diluted with BR (200 ml), extracted with ER and the organic phase washed with $H_2O$ (200 ml), BR (200 ml), dried and evaporated under reduced pressure to give the title alcohol as a yellow oil, (7.16 g). T.l.c. [G] Rf 0.73.

INTERMEDIATE 6

6-(4-Phenylbutoxy)hexanal

Pyridinium chlorochromate (4.1 g) was added to a solution of Intermediate 5 (3 g) in $CH_2Cl_2$ (25 ml). The mixture was stirred at RT for 0.75 h, triturated with ER (75 ml), and filtered through hyflo. The filtrate was evaporated and the residue dissolved in ER (50 ml), filtered through silica and evaporated under reduced pressure to give a pale yellow oil. Purification by [FCS] (120 g) [B] gave the title compound as a colourless oil (1.65 g). T.l.c. [B] Rf 0.3.

INTERMEDIATE 7

N-[6-(4-Phenylbutoxy)hexyl]benzenemethanamine

A solution of benzylamine (16.64 g) and Intermediate 3 (11.27 g) in THF (45 ml) was kept at RT for 4 days, diluted with ER (450 ml), filtered and the filtrate evaporated to give a colourless oil which was purified by [FCS] [C] to give the title compound (9.94 g) as a colourless oil.

Analysis Found: C, 81.60; H, 10.1; N, 4.2. $C_{23}H_{33}NO$ requires C, 81.35; H, 9.80; N, 4.15%.

INTERMEDIATE 8

1-[4-Hydroxy-3-(hydroxymethyl)phenyl]-2-[6-(4-phenylbutoxy)hexyl](phenylmethyl)amino]ethanone A solution of 2-bromo-1-[4-hydroxy-3-(hydroxymethyl)phenyl]ethanone (1 g), Intermediate 7, (1.4 g) and N,N-diisopropylethylamine (0.8 g) in THF (10 ml) was kept at 23° for 3 days. The mixture was diluted with ER (60 ml), washed with 8% $NaHCO_3$ (50 ml) and BR (50 ml), dried and evaporated in vacuo to give an oil. Purification by [FCS] (40 g) [D] afforded the title compound as a viscous yellow oil (1.68 g). T.l.c. [D] Rf 0.42.

INTERMEDIATE 9

2-Bromo-1-(2,2-dimethyl-1,3-benzodioxan-6-yl)ethanone

2-Methoxypropene (10 g) was added over 15 min to a stirred solution of 2-bromo-1-[4-hydroxy-3-(hydroxymethyl)phenyl]ethanone (5 g) and toluene-4-sulphonic acid (0.5 g) in $CH_2Cl_2$ (100 ml) at 23°. The mixture was stirred for 3 h, filtered through a wad of triethylamine-deactivated silica and evaporated to give an oil. Purification by [FCTS] (300 g) [E] afforded the title compound as an oil (4.8 g) which solidified on cooling. A small sample was crystallised from light petroleum (b.p. 60°-80°) to give white crystals m.p. 47°-48°.

INTERMEDIATE 10

1-(2,2-Dimethyl-1,3-benzodioxan-6-yl)-2-[6-(4-phenylbutoxy)hexyl](phenylmethyl)amino]ethanone A solution of Intermediate 9 (1.6 g), Intermediate 7 (2.1 g) and N,N-diisopropylethylamine (1.2 g) in THF (15 ml) was kept at 23° for 2 days. The mixture was diluted with EA (80 ml) washed with 8% $NaHCO_3$ (50 ml) and BR (50 ml), dried ($Na_2SO_4$) and evaporated in vacuo to give a yellow oil. Purification by [FCS] (150 g) [F] gave the title compound as a pale-yellow oil (2.2 g). T.l.c. [F] Rf 0.27.

INTERMEDIATE 11

6-(4-Phenylbutoxy)hexanoic acid

A mixture of Intermediate 5 (4 g) and pyridinium dichromate (21.04 g) in DMF (50 ml) was stirred at RT for 15 h, diluted with $H_2O$ (300 ml) and extracted with ER (2×100 ml). The extract was washed with $H_2O$ (2×250 ml), dried, filtered through a bed of silica and evaporated in vacuo to give a colourless oil. Purification by [FCS] (80 g) [F] gave the title compound as a colourless oil (0.85 g). T.l.c. [F] Rf 0.27.

INTERMEDIATE 12

N-[2-Hydroxy-2-[4-hydroxy-3-(hydroxymethyl)phenyl]ethyl]-1-(4-phenylbutoxy)hexanamide DMF (0.003 ml) and thionyl chloride (0.51 ml) were added to a solution of Intermediate 11 (0.89 g) in dry $CH_2Cl_2$ (17 ml). The resultant solution was stirred at RT for 2.5 h and evaporated to dryness to give the acid chloride. Intermediate 1 (0.934 g) in THF was treated with ethyl (trimethylsilyl)acetate (3.57 ml). Tetrabutyl ammonium fluoride (0.9 ml) was added dropwise to the stirred suspension at 0°. The resulting solution was stirred at RT for 2 h and added to a solution of the above acid chloride in THF (10 ml) under an atmosphere of nitrogen. Triethylamine (3.4 ml) was then added and the solution stirred at RT for 4 h, left to stand overnight, added to 2N hydrochloric acid (30 ml) and stirred for 15 min. The product was extracted into EA (3×25 ml) the extracts were washed with $H_2O$ (25 ml), 8% $NaHCO_3$ solution (25 ml) and BR (25 ml). The dried ($Na_2SO_4$) organic layer was evaporated to dryness to give a brown oil which was chromatographed on silica (Merck art 7754, 40 g) [H] to give a pale yellow oil. The dried oil solidified to give the title amide as an off white solid (1.06 g), m.p. 96°-97.5°.

INTERMEDIATE 13

6-(4-Phenylbutoxy)hexanamine

Intermediate 7 (25 g) in absolute ethanol (250 ml) was hydrogenated over palladium on carbon (1 g) and platinum on carbon (1 g) catalysts. The mixture was filtered through Hyflo and evaporated under reduced pressure to give the title amine as a colourless oil (16.49 g). T.l.c. $EN(CH_3OH)$ Rf 0.3.

INTERMEDIATE 14

Methyl 2-hydroxy-5-[[[6-(4-phenylbutoxy)hexyl]imino]acetyl]-benzoate

A solution of Intermediate 13 (0.49 g) in methanol (5 ml) was added over 15 min to a stirred suspension of methyl 5-(dihydroxyacetyl)-2-hydroxybenzoate in methanol (10 ml) at 23°. The mixture was stirred for 10 min, evaporated in vacuo and the residue purified by [FCTS] (40 g) [G] to give the title imine as a dark-orange oil (0.61 g). The imine was unstable and should be used promptly after preparation.

T.l.c. EN[G] Rf 0.37.

INTERMEDIATE 15

α-(Bromomethyl)-2,2-dimethyl-4H-1,3-benzodioxin-6-methanol

NaBH$_4$ (0.1 g) was added to a stirred solution of Intermediate 9 (0.6 g) in ethanol (20 ml) at 0°. The mixture was stirred at 0° for 1 h, diluted with H$_2$O (50 ml) and extracted with EA (2×25 ml). The extract was washed with BR (25 ml) dried and evaporated to give an oil which on trituration with HX afforded the title bromohydrin as a white solid (0.55 g) m.p. 84°–85° unchanged on recrystallisation from HX.

INTERMEDIATE 16

2,2-Dimethyl-6-oxiranyl-4H-1,3-benzodioxin

A mixture of Intermediate 15 (0.45 g), methanol (10 ml) and anhydrous K$_2$CO$_3$ (0.25 g) was stirred at 23° for 2 h. The mixture was diluted with ER (50 ml) filtered through a small wad of silica and evaporated in vacuo. The residual oil was dissolved in ER (50 ml), dried and evaporated to give the title epoxide as an oil (0.27 g).

T.l.c. (CX-EA 7:3) Rf 0.56.

INTERMEDIATE 17

[4-(2-Propynyloxy)butyl]benzene

A mixture of propargyl alcohol (10.0 g), (4-bromobutyl)benzene (38.0 g), aqueous NaOH (80 ml, 50% w/v), and tetrabutylammonium bisulphate (1.0 g) was stirred vigorously for 3 days, treated with H$_2$O (100 ml) and extracted with ER (2×200 ml). The dried extract was evaporated and the residue was purified on a column of silica (Merck 9385; 500 ml) [H] to give the title compound as a colourless oil (18.3 g). T.l.c. [A] Rf 0.2.

INTERMEDIATE 18

[[4-(6-Chloro-2-hexynyl)oxy]butyl]benzene

Intermediate 17 (15.0 g) was added dropwise to a suspension of lithamide from lithium (0.61 g) in liquid ammonia (50 ml) at −33°. The mixture was stirred for 2 h and bromochloropropane (13.9 g) in ER (10 ml) was added dropwise. The resulting suspension was stirred at −33° for 3 h and ammonia was allowed to evaporate overnight. The residue was treated cautiously with H$_2$O (30 ml) and extracted with ER (3×50 ml). The dried extract was evaporated and the residue was distilled to give the title compound as a colourless oil (12.9 g) b.p. 140°–150°/0.3 mmHg.

T.l.c. [A] Rf 0.2.

INTERMEDIATE 19

[[4-(6-Iodo-2-hexynyl)oxy]butyl]benzene

A mixture of Intermediate 18 (12.0 g) sodium iodide (20.0 g), and butanone (50 ml) was refluxed for 6 h and stirred at RT for 2 days, filtered and evaporated. The residue was dissolved in ER (50 ml) and washed with H$_2$O (50 ml) and aqueous sodium thiosulphate (50 ml). The dried organic phase was evaporated to leave the title compound as a pale yellow oil (12.6 g).

INTERMEDIATE 20

4-Hydroxy-α$^1$-[[[6-(4-phenylbutoxy)-4-hexynyl]amino]methyl]-1,3-benzenedimethanol Intermediate 19 (8.66 g) was added dropwise to a solution of Intermediate 1 (6.7 g) and N,N-diisopropylethylamine (3.9 g) in DMF (250 ml) at 70°. The mixture was heated at 70° for 2 h and DMF was removed under reduced pressure. The residue was treated with aqueous NaHCO$_3$ (1M; 200 ml) and extracted with EA (3×250 ml). The dried extract was evaporated and the residue was purified on a column of silica (Merck 9385; 250 ml) [I] to give a yellow oil. Trituration of the oil with ER gave the title compound as a white solid (4.3 g), m.p. 89°–90°.

T.l.c. [M] Rf 0.2.

INTERMEDIATE 21

3-[[(6-Bromohexyl)oxy]propyl]benzene

3-Phenylpropanol (3.00 g) and 1,6-dibromohexane (16.10 g, 10.2 ml) were stirred rapidly at RT with tetra-n-butylammonium hydrogen sulphate (0.5 g) and 12.5M aqueous NaOH (16 ml) for 30 h. The mixture was diluted with H$_2$O (80 ml), extracted with ER (3×100 ml), and the combined organic extracts were washed consecutively with H$_2$O (80 ml) and BR (80 ml). The dried extracts were evaporated and the residual oil purified by [FCS], eluting with CX (one columnful), followed by EA-CX (1:20) to give the title compound (5.35 g) as a colourless oil.

Analysis Found: C, 60.25; H, 7.8; Br, 26.45. C$_{15}$H$_{23}$BrO requires C, 60.2; H, 7.75; Br, 26.7%.

INTERMEDIATE 22

N-[6-(3-Phenylpropoxy)hexyl]benzenemethanamine hydrobromide

Intermediate 21 (317 g) was added to benzylamine (1116 ml) at a temperature of 115°–125° with stirring under nitrogen. Excess benzylamine was removed by distillation under reduced pressure. The residue was treated with methyl isobutyl ketone (1280 ml), the temperature adjusted to 50° and 47% w/v hydrobromic acid (115 ml) in H$_2$O (800 ml) was added at 50°–55°. The aqueous phase was removed and the organic solution was washed with H$_2$O (3×800 ml) at 50°. Distillation under reduced pressure and crystallisation of the residue from propan-2-ol afforded the title compound salt (318 g), m.p. 135°–136°.

INTERMEDIATE 23

Methyl 2-hydroxy-5-[[(phenylmethyl)[6-(3-phenylpropoxy)-hexyl]amino]acetyl]benzoate A solution of N,N-diisopropylethylamine (9.93 g) in CH$_2$Cl$_2$ (15 ml) was added to a solution of methyl 5-bromoacetyl-2-hydroxybenzoate (10 g) and Intermediate 22 (14.87 g) in CH$_2$Cl$_2$ (256 ml) at 16°. The solution was stirred under nitrogen for 23 h at 20°, washed with H$_2$O (5×100 ml), dried and filtered. This solution of the title compound was used without further purification. T.l.c. (ER) Rf 0.7.

INTERMEDIATE 24

1-[4-[(6-Bromohexyl)oxy]butyl]-2-methoxybenzene

NaH (46% dispersion in oil; 1.36 g) was added portionwise to a solution of 2-methoxybenzenebutanol (5.0 g) and 1,6-dibromohexane (13.8 g) in THF (50 ml). The suspension was refluxed for 20 h and was treated cautiously with H$_2$O (20 ml). The resulting emulsion was extracted with ER (2×50 ml) and the dried extract was evaporated to leave a yellow oil. The oil was purified on a column of silica (Merck 9385, 600 ml) [A] to give the title compound as a colourless oil (5.6 g). T.l.c. [B] Rf 0.2.

INTERMEDIATE 25

Benzenehexanol (3-Bromopropyl)benzene (20 g) in THF (75 ml) was added dropwise to magnesium (2.43 g) at a rate to maintain gentle reflux. The mixture was stirred for 2 h at RT and oxetane (10 g) was added dropwise. The resulting suspension was stirred at RT for 2 h and at reflux for 16 h and poured into saturated aqueous NH$_4$Cl (100 ml). The mixture was extracted with ER (3×75 ml) and the dried extract was evaporated to leave a yellow oil. Distillation of the oil gave the title compound as a colourless liquid (6.05 g) b.p. 100°–105°/0.4 mmHg. T.l.c. [O] Rf 0.3.

INTERMEDIATE 26

2-[(4-Chlorobutyl)oxy]tetrahydropyran

Dihydropyran (15.5 g) was added dropwise to a mixture of 4-chlorobutanol (20 g) and hydrochloric acid (18M, 1 drop) at RT. The mixture was stirred for 30 min and washed with H$_2$O (100 ml), aqueous NaHCO$_3$ (1M, 50 ml) and BR (50 ml). The dried liquid was heated under reduced pressure to leave the title compound as a colourless liquid (31.9 g). T.l.c. [L] Rf 0.5.

INTERMEDIATE 27

2-[[4-[(6-Phenylhexyl)oxy]butyl]oxy]tetrahydropyran

NaH (3.85 g) was added portionwise to a mixture of Intermediate 25 (5.5 g), Intermediate 26 (30 g), potassium iodide (1 g) and THF (50 ml). The mixture was refluxed for 28 h and treated cautiously with H$_2$O (100 ml). The resulting emulsion was extracted with ER (3×100 ml) and the dried extract was evaporated to leave a yellow oil. Excess of Intermediate 26 was distilled from the mixture at 80°/0.4 mmHg and the residue was purified on a column of silica (300 ml) [B] to give the title compound as a colourless oil (2.7 g). T.l.c. [B] Rf 0.25.

INTERMEDIATE 28

4-[(6-Phenylhexyl)oxy]butan-1-ol

A solution of Intermediate 27 (2.65 g) in methanol (20 ml) and 80% acetic acid (10 ml) was stirred at RT for 20 h. The solution was basified with aqueous NaOH (2M). The mixture was refluxed for 2 h and methanol was evaporated. The resulting emulsion was extracted with ER (2×50 ml) and the dried extract was evaporated to leave the title compound as a colourless oil (2.0 g). T.l.c. [O] Rf 0.3.

INTERMEDIATE 29

4-[(6-Phenylhexyl)oxy]butan-1-ol methanesulphonate

Methanesulphonyl chloride (0.4 g) was added dropwise to a solution of Intermediate 28 (0.8 g) and triethylamine (0.5 g) in CH$_2$Cl$_2$ (5 ml) at 0°. The mixture was stirred at RT for 25 min and filtered. The filtrate was washed with saturated aqueous NaHCO$_3$ (20 ml) and BR (20 ml). The dried (Na$_2$SO$_4$) organic phase was evaporated to leave the title compound as a yellow oil (1.0 g).

INTERMEDIATE 30

2-[2-[(6-Bromohexyl)oxy]ethyl]-1,3-dimethylbenzene

NaH (46% dispersion in oil; 4.2 g) was added portionwise to a solution of 2,6-dimethylbenzeneethanol (6.0 g) and 1,6-dibromohexane (19.52 g) in THF (50 ml) under nitrogen. The mixture was refluxed for 18 h and treated cautiously with H$_2$O (20 ml). The resulting emulsion was extracted with ER (3×100 ml) and the dried extract was evaporated to leave a yellow oil. Excess 1,6-dibromohexane was removed under reduced pressure and the residue was purified on a column of silica (300 ml) [B] to give the title compound as a colourless oil (6.6 g) b.p. 110°–115°/0.4 mmHg.

The following intermediates were prepared in a similar manner to Intermediate 21.

INTERMEDIATE 31

4-[[(6-Bromohexyl)oxy]butyl]-1-methoxybenzene (3.3 g), b.p. 180°–190°/0.5 torr, from 1,6-dibromohexane (8 g) and 4-(4-methoxyphenyl)butanol (2 g).

INTERMEDIATE 32

5-[[(5-Bromopentyl)oxy]pentyl]benzene (3.2 g), b.p. 185°–195°/0.3 torr, from 1,5-dibromopentane (8.5 g) and benzenepentanol (2 g).

INTERMEDIATE 33

1-[2-[(6-Bromohexyl)oxy]ethyl-4-chlorobenzene (4.0 g), b.p. 169°/0.8 torr, from 1,6-dibromohexane (8.65 g) and 4-chlorobenzeneethanol (3.0 g).

INTERMEDIATE 34

1-[3-[(6-Bromohexyl)oxy]propyl]-4-fluorobenzene (2.22 g), b.p. 170°/0.7 torr, from 1,6-dibromohexane (8.82 g) and Intermediate 42 (2.0 g).

INTERMEDIATE 35

[2-[(8-Bromooctyl)oxy]ethyl]benzene (4.3 g), T.l.c. [B] Rf 0.3, from 1,8-dibromooctane (13.4 g) and benzeneethanol (20 g).

INTERMEDIATE 36

[5-[6-(Bromohexyl)oxy]pentyl]benzene (2.7 g), T.l.c. [B] Rf 0.3, from 1,6-dibromohexane (9.0 g) and benzenepentanol (2.0 g).

INTERMEDIATE 37

1-[2-[(6-Bromohexyl)oxy]ethyl]-4-ethylbenzene (2.6 g), T.l.c. [B] Rf 0.25, from 1,6-dibromohexane (9.8 g) and 4-ethylbenzeneethanol (2.0 g).

INTERMEDIATE 38

[3-[(7-Bromoheptyl)oxy]propyl]benzene (2.05 g) from 1,7-dibromoheptane (3.83 g) and 3-phenylpropanol (1.08 ml).

Analysis Found: C,62.6;H,8.4. C$_{16}$H$_{25}$BrO requires C,61.35;H,8.05%.

INTERMEDIATE 39

5-[4-[(6-Bromohexyl)oxy]butyl]-1,3-benzodioxolane (3.2 g), T.l.c. (CX-EA 4:1) Rf 0.43, from 1,6-dibromohexane (9.5 g) and Intermediate 44 (2.5 g).

INTERMEDIATE 40

1-[2-[(6-Bromohexyl)oxy]ethyl]-3-chlorobenzene (4.12 g), T.l.c. (ER- HX 1:79) Rf 0.16, from 1,6-dibromohexane (11.71 g) and 3-chlorobenzeneethanol (2.5 g).

INTERMEDIATE 41

1-[3-[(6-Bromohexyl)oxy]propyl]-2-fluorobenzene (4.71 g), T.l.c. (ER- CX 1:79) Rf 0.22, from 1,6-dibromohexane (14.28 g) and 3-(2-fluorophenyl)-1-propanol (3.0 g).

INTERMEDIATE 42

4-Fluorobenzenepropanol

A Grignard reagent was prepared from 4-bromo-1-fluorobenzene (8.0 g), magnesium turnings (1.10 g), and iodine (one small crystal) in THF (40 ml). Oxetane (2.3 g) in THF (10 ml) was added at RT and the reaction mixture was heated at reflux overnight. The cooled solution was poured into aqueous saturated $NH_4Cl$ (100 ml), extracted with ER (2×150 ml) and the combined, dried ($Na_2SO_4$) extracts were evaporated. The residual oil was purified by flash chromatography over silica gel (Merck 9285, 5.0 cm wide column), eluting with ER-CX (1:5→1:3). The resultant oil was further purified by distillation to give the title compound (3.15 g) as a colourless oil, b.p. 150°/0.8 torr.

INTERMEDIATE 43

(E/Z)-4-[1,3-Benzodioxol-5-yl]-3-butenol, (E:Z=3:2)

A solution of n-butyllithium in HX (1.6M, 6.5 ml) was added over 5 min to a stirred suspension of [3-(1-methoxy-1-methylethoxy)propyl]triphenylphosphonium bromide (4.8 g) in dry THF (25 ml) at 0° under nitrogen. The mixture was stirred at 0° for 45 min, treated with a solution of piperonal (1.2 g) in dry THF (5 ml) and stirred at 0° to 23° over 1 h. ER (70 ml) was added, the mixture filtered through silica and the filtrate evaporated in vacuo to give a yellow oil which was dissolved in a mixture of $THF-H_2O$-2M hydrochloric acid 25:5:1 (31 ml) and kept at 23° for 0.5 h. The mixture was diluted with 8% $NaHCO_3$ (30 ml), extracted with ER (2×50 ml) and the extract was washed with BR (50 ml), dried and evaporated in vacuo to afford the title alcohol as a yellow oil (1.05 g) (E:Z ratio of 3:2). T.l.c. [O] Rf 0.22.

INTERMEDIATE 44

1,3-Benzodioxole-5-butanol

A solution of Intermediate 43 (3.5 g) in absolute ethanol (50 ml) was hydrogenated at RT and atmospheric pressure over 10% palladium on carbon catalyst (200 mg). Hydrogen absorption (392 ml) ceased after 45 min, the solution was filtered and the filtrate evaporated in vacuo to give the title alcohol as a colourless oil (3.5 g). T.l.c. (EA-CX (3:2)) Rf 0.49.

The following intermediates were prepared in a similar manner to Intermediate 21.

INTERMEDIATE 45

[4-(4-Bromobutoxy)butyl]benzene (2.44 g), T.l.c. [K] Rf 0.68, from 1,4-dibromobutane (8.6 g) and benzenebutanol (2 g).

INTERMEDIATE 46

[5-(4-Bromobutoxy)pentyl]benzene (2.46 g), T.l.c. [K] Rf 0.58 from 1,4-dibromobutane (7.89 g) and benzenepentanol (2 g).

INTERMEDIATE 47

[2-[(7-Bromoheptyl)oxy]ethyl]benzene (6.2 g), T.l.c. (CX-ER 40:1) Rf 0.29, from 1,7-dibromoheptane (10.5 g) and benzeneethanol (50.0 g).

INTERMEDIATE 48

1-[2-[(5-Bromopentyl)oxy]ethyl]-4-ethylbenzene (2.19 g) T.l.c. [K] Rf 0.48, from 1,5-dibromopentane (7.8 g) and 4- ethylbenzeneethanol (1.7 g).

INTERMEDIATE 49

1-[2-[(6-Bromohexyl)oxy]ethyl]-4-methylbenzene (8.51 g) T.l.c. [K] Rf 0.56 from 1,6-dibromohexane (24.2 g) and 4- methylbenzeethanol (4.5 g).

INTERMEDIATE 50

[2-(4-Bromobutoxy)ethyl]benzene (2.85 g), T.l.c. [K] Rf 0.41, from 1,4-dibromobutane (10.6 g) and benzeneethanol (2 g).

INTERMEDIATE 51

[2-[(5-Bromopentyl)oxy]ethyl]benzene (3.8 g), T.l.c. [K] Rf 0.46 from 1,5-dibromopentane (11.3 g) and benzeneethanol (2 g).

INTERMEDIATE 52

[3-[(5-Bromopentyl)oxy]propyl]benzene (2.8 g), T.l.c. [K] Rf 0.44 from 1,5-dibromopentane (10.2 g) and benzenepropanol (2 g).

INTERMEDIATE 53

[4-[(5-Bromopentyl)oxy]butyl]benzene

4-Phenylbutanol (5.80 g) was stirred in 1,5-dibromopentane (52 ml) and 5N NaOH solution (50 ml), and tetrabutyl ammonium bisulphate (0.87 g) was added and the reaction mixture was stirred at RT for 72 h. (After 42 h the NaOH layer was replaced by a fresh solution). The two layers were separated and the aqueous phase was extracted with ER (3×50 ml). The combined organic layers were dried ($Na_2SO_4$), and evaporated to give a clear liquid. Excess 1,5-dibromopentane was removed by distillation at 60° 1.00 mmHg. The residue was chromatographed on a silica (70–230 mesh, 30 g) column using CX as eluant, with a slowly increasing quantity of ER until the title compound was obtained, which on evaporation gave a colourless oil (3.26 g). T.l.c. (CX-ER (99:1)) Rf 0.15.

INTERMEDIATE 54

1-[2-[(6-Bromohexyl)oxy]ethyl]-4-methoxybenzene

4-Methoxybenzeneethanol (5.0 g) and 1,6-dibromohexane (23.7 g) were stirred rapidly at RT with tetra-n-butyl ammonium bisulphate (0.94 g) and 12.5M aqueous NaOH (30 ml) for 16 h. The mixture was diluted with H₂O (125 ml), extracted with ER (3×150 ml) and the combined organic extracts were washed consecutively with H₂O (125 ml), BR (125 ml), dried and evaporated to give an oil (24.6 g). The oil was purified by [FCS] eluting with ER-CX (0:100→4:96) to give the title compound as a colourless oil (8.30 g). T.l.c. (CX-ER (40:1)) Rf 0.33.

INTERMEDIATE 55

7-[2-(Phenylethoxy)]-2-heptanone

A solution of Intermediate 51 (2.0 g) in ER (15 ml) was added dropwise to magnesium (0.18 g). The mixture was refluxed for 1 h, cooled and added during 40 min to acetic anhydride (1.4 g) in ER (10 ml) at −78°. The suspension was stirred at −78° for 2 h, warmed to −10° and treated with saturated aqueous NH₄Cl (20 ml). The mixture was extracted with ER (2×25 ml) and the extract was washed with 5% NaOH (20 ml) and BR (20 ml). The dried extract was evaporated and the residue was purified on a column of silica (100 ml) [L] to give the title compound as a colourless oil (0.70 g). T.l.c. [L] Rf 0.25.

The following ketones were prepared in a similar manner: (Intermediates 57, 62 and 64 are described after Intermediate 65)

INTERMEDIATE 56

7-[4-(Phenylbutoxy)]-2-heptanone (1.15 g) from Intermediate 53 (3.0 g) and acetic anhydride (2 g). T.l.c. [L] Rf 0.25.

INTERMEDIATE 58

6-(3-Phenylpropoxy)-2-hexanone (1.3 g) from Intermediate 57 (3.5 g) and acetic anhydride (2.6 g). T.l.c. [L] Rf 0.25.

INTERMEDIATE 59

6-(4-Phenylbutoxy)-2-hexanone (1.3 g) from Intermediate 45 (3.0 g) and acetic anhydride (2.3 g). T.l.c. [L] Rf 0.35.

INTERMEDIATE 60

8-(2-Phenylethoxy)-3-octanone (4.35 g) from Intermediate 51 (7.0 g) and propionic anhydride (6.53 g). T.l.c. (CX-ER 7:1) Rf 0.22.

INTERMEDIATE 61

9-(2-Phenylethoxy)-4-nonanone (2.25 g) from Intermediate 51 (5.0 g) and butyric anhydride (6.75 g). T.l.c. [B] Rf 0.2.

INTERMEDIATE 63

7-[2-(4-Fluorophenyl)ethoxy]-2-heptanone (1.88 g) from Intermediate 62 (6.0 g) and acetic anhydride (4.2 g), b.p. 172°/0.7 Torr.

INTERMEDIATE 65

7-[3-(4-Methoxyphenyl)propoxy]-2-heptanone (2.17 g) from Intermediate 64 (5.5 g) and acetic anhydride (3.66 g). T.l.c. [F] Rf 0.18.

INTERMEDIATE 57

[[3-(4-Bromobutoxy)]propyl]benzene

A mixture of 3-phenylpropanol (2 g), tetrabutylammonium bisulphate (0.5 g) 1,4-dibromobutane (9.5 g) and 50% NaOH (11 ml) was stirred at RT for 22 h, diluted with H₂O (250 ml) and extracted with ER (250 ml). The organic phase was washed successively with H₂O (250 ml) and BR (250 ml), dried and evaporated under reduced pressure to give a colourless oil. Purification by [FCS] [120 g], eluting with CX followed by [K] afforded the title compound as a colourless oil (2.72 g).

T.l.c. (CX - EA 1:9) Rf 0.51.

INTERMEDIATE 62

1-[2-[(5-Bromopentyl)oxy]ethyl]-4-fluorobenzene

4-Fluorobenzeneethanol (10.0 g), 1,5-dibromopentane (29 ml), tetra-n-butylammonium hydrogen sulphate (3.2 g, 9 mmol), and aqueous 12.5M NaOH (109 ml) were stirred vigorously at RT overnight. The mixture was diluted with H₂O (400 ml), extracted with ER (3×200 ml), and the combined organic extracts were evaporated. The residual oil was purified by [FCS] eluting with CX - ER (100:0→100:6), to give the title compound as a colourless oil (14.37 g). T.l.c. (ER-CX, 19:1) Rf 0.22.

INTERMEDIATE 64

1-[3-[(5-Bromopentyl)oxy]propyl]-4-methoxybenzene

4-Methoxybenzenepropanol (7.5 g) and 1,5-dibromopentane (30.5 g) were stirred rapidly at RT with tetra-n-butylammonium bisulphate (1.02 g) and 12.5M aqueous NaOH (36 ml) for 16 h. The mixture was diluted with H₂O (170 ml), extracted with ER (3×200 ml) and the combined organic extracts were washed consecutively with H₂O (170 ml) and BR (170 ml), dried and evaporated to give an oil (34.8 g). The oil was purified by [FCS] eluting with ER - CX (0:100→4:96) to give the title compound as a colourless oil (8.83 g). T.l.c. (CX-ER 79:1) Rf 0.1.

INTERMEDIATE 66

1,1-Dimethyl-5-(3-phenylpropoxy)-2-pentynamine 1,1-Dimethylpropargylamine (8.5 g) was added dropwise to a suspension of lithamide [from lithium (1.7 g)] in liquid ammonia (100 ml) at −33°. The mixture was stirred for 90 min and a solution of [3-(2-bromoethoxy)propyl]benzene (21.5 g) in ER (30 ml) was added dropwise. The suspension was stirred for 4 h and ammonia was allowed to evaporate overnight. The residue was treated with H₂O (100 ml) and extracted with ER (3×100 ml). The dried extract was evaporated and the residue was distilled to give the title compound as a colourless oil (3.0 g) b.p. 160°-165°/0.2 mmHg. T.l.c. (ER) Rf 0.3.

INTERMEDIATE 67

α¹-[[[1,1-Dimethyl-5-(3-phenylpropoxy)-2,E-pentenyl]amino]methyl]-4-hydroxy-1,3-benzenedimethanol A solution of methyl 5-(bromoacetyl)-2-hydroxybenzoate (3.3 g) Intermediate 66 (2.9 g) and N,N-diisopropylethylamine (1.55 g) in EA (50 ml) was refluxed for 3 h, filtered and evaporated. The residue was dissolved in ER (50 ml), filtered, and added dropwise to a suspension of LiAlH₄ (2 g) in ER (100 ml) at 0° under nitrogen. The mixture was stirred at 0° for 1 h at RT for 1 h and was treated cautiously with H₂O (10 ml). The mixture was acidified to pH 1 with hydrochloric acid (2M), and basified with solid KHCO₃ to pH8. The ER layer was decanted off and the aqueous slurry was extracted with CHCl₃ (3×500 ml). The dried extract was evaporated to leave an orange oil. The oil was purified on a column of silica (300 ml) eluted with EA - methanol - triethylamine (93:7:1) to give the title compound as a white solid (0.88 g) m.p. 108°-109°. T.l.c. [M] Rf 0.25.

INTERMEDIATE 68

1,1-Dimethyl-7-(2-phenylethoxy)heptanoic acid n-Butyllithium in HX (1.6M; 172 ml) was added dropwise to diisopropylamine (27.5 g) in THF (40 ml) at −78° under nitrogen. The mixture was warmed to 0°, stirred for 45 min, and isobutyric acid (12.0 g) was added dropwise. The resulting suspension was stirred at RT for 4 h and Intermediate 51 (25.0 g) was added dropwise. The mixture was stirred for 16 h at RT, treated slowly with hydrochloric acid (2M; 350 ml), and extracted with ER (2×250 ml). The dried extract was evaporated and the residue was purified on a column of silica (Merck 9385; 300 ml) [B] to give the title compound as a colourless oil (17.0 g). T.l.c. [L] Rf 0.35.

INTERMEDIATE 69

1-1-Dimethyl-6-(2-phenylethoxy)hexylcarbamic acid, phenylmethyl ester

Ethyl chloroformate (3.26 g) in acetone (10 ml) was added to a solution of Intermediate 68 (8.0 g) and triethylamine (3.03 g) in acetone (100 ml) and H₂O (10 ml) at 0°. The mixture was stirred for 40 min at 0° and sodium azide (2.25 g) in H₂O (25 ml) was added dropwise. The resulting suspension was stirred at RT for 30 min, diluted with H₂O (200 ml), and extracted with toluene (2×200 ml). The dried (Na₂SO₄) extract was evaporated to half-volume, heated at 70°-80° for 2 h, and toluene was removed under reduced pressure. The resulting isocyanate in benzyl alcohol (20 ml) was heated at 80°-83° for 60 h and benzyl alcohol was removed under reduced pressure (1 Torr). The residue was purified in a column of silica (Merck 9385; 300 ml) eluted with CX - ER (17:3) to give the title compound as a colourless oil (7.45 g). T.l.c. [L] Rf 0.25.

INTERMEDIATE 70

1,1-Dimethyl-6-(2-phenylethoxy)hexanamine

A solution of Intermediate 69 (6.8 g) in ethanol (100 ml) was hydrogenated over 10% palladium on charcoal (0.5 g) for 40 min filtered, and evaporated to give the title compound as a colourless oil (4.3 g).

INTERMEDIATE 71

Methyl 5-[2-(dimethylamino)-1-hydroxyethyl]-2-(phenylmethoxy)benzoate

Dimethylamine (33% in ethanol, 156 ml) was added to a stirred suspension of methyl 5-(bromoacetyl)-2-(phenylmethoxy)benzoate (105.8 g) in absolute ethanol (1 l) and THF (1 l). The resulting solution was stirred at RT for 2 h, treated with NaBH₄ (25 g) and stirred at RT overnight. The solvent was removed in vacuo and H₂O (500 ml) was added to the residue. The mixture was extracted with EA (2×500 ml), the combined extracts were washed with H₂O and BR, dried (Na₂SO₄) and concentrated in vacuo. The product was purified twice by [FCS] eluted with EA-methanol-triethylamine (80:20:1) to give the title compound as a fawn solid (59.8 g) m.p. 79°-81°.

INTERMEDIATE 72

(R)-Methyl 5-[2-(dimethylamino)-1-hydroxyethyl]-2-(phenylmethoxy)benzoate[S-(R*,R*)-2,3-bis[(4-methylbenzoyl)oxy]butanedioate (1:1) (salt)

Intermediate 71 (50 g) in hot methanol (250 ml) was mixed with (−)-di-p-toluoyl tartaric acid, monohydrate (60 g) in hot methanol (250 ml). The resulting precipitate was collected by filtration and recrystallised three times from methanol (25 ml/gram) to give the title compound as white needles (16.4 g). m.p. 169°-170° $[\alpha]_D^{18.2°} -103.3°$ (c 0.51 in CH₃OH).

INTERMEDIATE 73

(R)-Methyl 5-[2-(dimethylamino)-1-hydroxyethyl]-2-(phenylmethoxy)benzoate

Intermediate 72 (16.4 g) was partitioned between EA (175 ml) and 6N ammonium hydroxide (8.4 ml) in H₂O (175 ml). The organic layer was washed with 8% NaHCO₃ (2×100 ml), BR, dried (Na₂SO₄) and concentrated in vacuo to give the title compound as a viscous oil (7.9 g) T.l.c. (EA-methanol-triethylamine 80:20:1) Rf=0.23.

INTERMEDIATE 74

(R)-β-Hydroxy-3-(methoxycarbonyl)-N,N,N-trimethyl-4-(phenylmethoxy) benzeneethanaminium iodide Intermediate 73 (7.85 g) and methyl iodide (17.5 ml) in acetone (55 ml) was stirred at reflux under nitrogen for 3 h. The acetone was removed in vacuo and CHCl₃ (100 ml) was added to the residue. The resulting precipitate was collected by filtration and dried in vacuo (12.2 g). Recrystallisation from methanol gave the title compound as an off-white solid (4.5 g) m.p. 85°-120° $[\alpha]_D^{20.2} -32.2°$ (c 0.7 in DMSO).

INTERMEDIATE 75

(R)-Methyl 5-oxiranyl-2-(phenylmethoxy)benzoate

A warm suspension of Intermediate 74 in dry acetonitrile (200 ml) was treated with tetramethylammonium fluoride-bi-methanol solvate (5.5 g) and stirred at reflux, with continuous removal of the distillate, for 2.5 h. The cooled reaction mixture was filtered and the filtrate was concentrated in vacuo to a semi-solid. Dry ER (100 ml) was added and the mixture was refiltered. The filtrate was concentrated to an oil which was purified by [FCS] eluting with CX-EA-triethylamine 80:20:1 to give the title compound as a colourless oil (1.98 g). $[\alpha]_D^{23.3°} +19.9°$ (c 0.86 in benzene).

T.l.c. (CX-EA-triethylamine 80:20:1) Rf=0.14.

INTERMEDIATE 76

(R)-Methyl 5-[1-hydroxy-2-[(phenylmethyl)[6-(3-phenylpropoxy)-hexyl]amino]ethyl]-2-(phenylmethoxy)benzoate Intermediate 75 (1.9 g) and Intermediate 22, free base (2.17 g) in methanol (50 ml) were stirred at reflux, under nitrogen, for 6 h. The solvent was removed in vacuo and the residual oil was purified by [FCS] eluting with CX-EA-triethylamine 75:25:1 to give the title compound as a pale yellow oil (2.1 g). $[\alpha]_D^{20.6°}$ −62.4° (c 0.74 in T.l.c.
(CX-EA-triethylamine 80:20:1) Rf=0.12.

INTERMEDIATE 77

(R)-(−)-4-(Phenylmethoxy)-$\alpha^1$-[[(phenylmethyl)[6-(3-phenylpropoxy)hexyl]amino]methyl]-1,3-benzenedimethanol Intermediate 76 (2.0 g) in dry THF (40 ml) was added to a stirred suspension of LiAlH$_4$ (300 mg) in dry THF (40 ml) at RT, under nitrogen. The reaction mixture was placed in an oil-bath, preheated to 80°, and stirred at reflux for 5 min. The cooled mixture was treated cautiously with H$_2$O (40 ml) and ER (40 ml). The phases were separated and the aqueous phase was re-extracted with ER (50 ml). The combined organic phases were washed with H$_2$O and BR, dried (Na$_2$SO$_4$) and concentrated in vacuo. [FCS] using CX-EA-triethylamine 66:33:1 as eluant gave the title compound as a clear, colourless oil (1.70 g). $[\alpha]_D^{21°}$ −64.6° (c 0.6 in CHCl$_3$) T.l.c. (CX-EA-triethylamine 66:33:1) Rf=0.15

EXAMPLE 1

4-Hydroxy-$\alpha^1$-[[[6-(2-phenylethoxy)hexyl]amino]methyl]-1,3-benzenedimethanol, hydrate A mixture of Intermediate 1 (0.93 g), Intermediate 2 (1.6 g), pyridine (1 ml) and DMF (25 ml) was left at RT for 2 weeks. The resulting solution was evaporated and the residue was purified on a column of silica (Merck 9385: 250 ml) [I] to give a yellow oil. The oil was triturated with ER to give the title compound as a cream solid (0.20 g) m.p. 89°–91°. T.l.c. [M] Rf 0.1.

EXAMPLE 2

4-Hydroxy-$\alpha^1$-[[[6-(4-phenylbutoxy)hexyl]amino]methyl]-1,3-benzenedimethanol A solution of Intermediate 1 (8.9 g), potassium iodide (4.0 g), triethylamine (5 ml) and DMF (250 ml) at 70° was treated dropwise with Intermediate 3 (7.5 g). The solution was heated at 65°–70° for 1 h and DMF was removed under reduced pressure. The residue was treated with H$_2$O (200 ml) and the resulting emulsion was extracted with EA (3×300 ml). The combined extracts were washed with H$_2$O (2×50 ml) and BR (50 ml), dried and evaporated. Trituration of the residue with ER/10% EA (200 ml) for 16 h gave a suspension from which the title compound was collected as a white solid (2.6 g), m.p. 75.5°–76.5°. T.l.c. [M] Rf 0.2.

EXAMPLE 3

4-Hydroxy-$\alpha^1$-[[[6-(4-phenylbutoxy)hexyl]amino]methyl]-1,3-benzenedimethanol A solution of Intermediate 4 (2.2 g) and Intermediate 6 (1.0 g) in absolute ethanol (25 ml) was hydrogenated at RT and atmospheric pressure over 10% palladium on carbon catalyst (0.2 g). The mixture was filtered through hyflo and evaporated to give an oil. Purification by [FCTS] (40 g) [N] gave an oil which on trituration with ER afforded the title compound as a white solid (0.77 g) m.p. 75°–76°, mixed m.p. 74°–76° with the product of Example 2. T.l.c. EN [N] Rf 0.31.

EXAMPLE 4

4-Hydroxy-$\alpha^1$-[[[6-(4-phenylbutoxy)hexyl)]amino]methyl]-1,3-benzenedimethanol Intermediate 6 (0.5 g) was added to a stirred suspension of Intermediate 1 (0.5 g) in methanol (5 ml) at 23°. The mixture was stirred for 0.5 h, NaBH$_4$ (0.5 g) was added and stirring continued for 7 h. The mixture was diluted with H$_2$O (50 ml), extracted with EA (2×25 ml) and the organic phase was washed with BR (25 ml), dried and evaporated to give an oil. Purification by [FCTS] (30 g) afforded an oil which on trituration with cold ER gave the title compound as a white solid (0.25 g), m.p. 76°–77°, mixed m.p. 75°–76° with the product of Example 2.
T.l.c. EN[N] Rf 0.31.

EXAMPLE 5

4-Hydroxy-$\alpha^1$-[[[6-(4-phenylbutoxy)hexyl](phenylmethyl)amino]methyl]-1,3-benzenedimethanol A solution of Intermediate 7 (51 g) and 4-bromoacetyl-2-(hydroxymethyl)phenol diacetate [prepared from 36.25 g of 4-acetyl-2-(hydroxymethyl)phenol diacetate] in CHCl$_3$ (410 ml) was stirred at the reflux for 24 h, cooled and concentrated under reduced pressure. The residual oil was dissolved in toluene (75 ml) and concentrated. The oil was dissolved in toluene (125 ml), washed with H$_2$O (150 ml) and BR (50 ml). The aqueous solutions were extracted with toluene (30 ml) and the combined extracts were washed with H$_2$O (50 ml) and concentrated. The crude ketoamine diacetate was stirred in ethanol (155 ml) and 10N hydrochloric acid (48 ml) in H$_2$O (58 ml) was added dropwise with stirring, the temperature being maintained below 20°. After being allowed to stand at 0° for 2 days the solution was treated with ethanol (180 ml) and NaOH (17.6 g) in H$_2$O (18 ml) whilst keeping the temperature below 15°. NaBH$_4$ (11.06 g) and NaOH (2.11 g) in H$_2$O were added, followed after 24 h by more NaBH$_4$ (9.5 g) over a period of 48 h. The mixture was neutralised with 2N sulphuric acid and concentrated to a slurry which was partitioned between 2N Na$_2$CO$_3$ (100 ml) and EA (200 ml). The organic layer was treated with a further quantity of 2N Na$_2$CO$_3$ (100 ml) and EA (200 ml). The combined organic extracts were washed, dried and evaporated. The crude triol was chromatographed on Sorbsil (700 g), [G] to give the title compound (26.5 g) identified by its n.m.r. spectrum.

EXAMPLE 6

4-Hydroxy-$\alpha^1$-[[[6-(4-phenylbutoxy)hexyl]amino]methyl]-1,3-benzenedimethanol A solution of Intermediate 8 (0.4 g) in absolute ethanol (25 ml) was hydrogenated at 23° and atmospheric pressure over 10% palladium on carbon (0.2 g) and 10% platinum on carbon (0.2 g) catalysts. The mixture was filtered through hyflo and evaporated to give an oil. Purification by [FCTS] (20 g) [N] afforded an oil which on trituration with ER gave the title compound as a white solid (0.21 g) m.p. 76.5°–77.5°, mixed m.p. 75.5°–76.5° with the product of Example 2. T.l.c. EN [N] Rf 0.31.

EXAMPLE 7

2,2-Dimethyl-α-[[[6-(4-phenylbutoxy)hexyl]amino]methyl]-4H-1,3-benzodioxin-6-methanol A solution of Intermediate 10 (1 g) in absolute ethanol (20 ml) was hydrogenated at 23° and atmospheric pressure over 10% palladium on carbon (0.1 g) and 10% platinum on carbon (0.1 g) catalysts. The mixture was filtered through hyflo and evaporated in vacuo to give an oil which slowly crystallised. The solid was slurried in HX, filtered off and dried to give the title compound as white crystals (0.72 g) m.p. 68°–70°. T.l.c. EN (EA - MeOH 19:1) Rf 0.45.

EXAMPLE 8

4-Hydroxy-α$^1$-[[[6-(4-phenylbutoxy)hexyl]amino]methyl]-1,3-benzenedimethanol

A solution of Intermediate 12 (0.3 g) in dry THF (5 ml) was added to a stirred suspension of LiAlH$_4$ (0.26 g) in dry THF (15 ml) at 0° under nitrogen. The mixture was stirred at 23° for 20 h, diluted cautiously with H$_2$O (30 ml), acidified to pH5 with 2M hydrochloric acid, basified to pH8 with NaHCO$_3$ and extracted with EA (3×50 ml). The organic phase was washed with BR (50 ml), dried (Na$_2$SO$_4$) and evaporated to give an oil which was purified by [FCTS] [N] to give an oil. Trituration with cold ER afforded the title compound as a white solid (0.064 g) m.p. 75°–76.5° mixed m.p. 75°–76° with the product of Example 2. T.l.c. EN[N] Rf 0.31.

EXAMPLE 9

4-Hydroxy-α$^1$-[[[6-(4-phenylbutoxy)hexyl]amino]methyl]-1,3-benzenedimethanol

A solution of Intermediate 13 (0.91 g) in THF (10 ml) was added over 15 min to a stirred solution of methyl 5-(bromoacetyl)-2-hydroxybenzoate (1 g) and N,N-diisopropylethylamine (0.85 g) in THF (10 ml) at 0°. The mixture was stirred at 0° for 2 h, diluted with ether (50 ml), washed with 0.5M hydrochloric acid (50 ml), 8% NaHCO$_3$ (50 ml), BR (50 ml), dried and evaporated to give an oil. Purification by [FCS] (60 g) [O] afforded the intermediate glycyl compound as an oil (0.6 g). A solution of this oil (0.6 g) in dry THF (5 ml) was added to a stirred slurry of LiAlH$_4$ (0.25 g) in dry THF (25 ml) under nitrogen at 23°. The mixture was stirred for 18 h, diluted cautiously with H$_2$O (50 ml), acidified to pH5 with 2M hydrochloric acid, basified to pH8 with NaHCO$_3$ and extracted with EA (2×100 ml). The dried extract was evaporated to give an oil which was purified by [FCTS] (20 g) [N] to give an oil on which trituration with ER afforded the title compound as a white powder (0.12 g) m.p. 75.5°–76.5°, mixed m.p. 75°–76° with the product of Example 2. T.l.c. EN [N] Rf 0.31.

EXAMPLE 10

4-Hydroxy-α$^1$-[[[6-(4-phenylbutoxy)hexyl]amino]methyl]-1,3-benzenedimethanol

A solution of Intermediate 14 (0.58 g) in dry THF (10 ml) was added over 10 min to a stirred suspension of LiAlH$_4$ (0.5 g) in dry THF (25 ml) at 0° under nitrogen. The mixture was stirred at 23° for 18 h, diluted cautiously with H$_2$O (50 ml), acidified to pH5 with 2M hydrochloric acid, basified to pH8 with NaHCO$_3$ and extracted with EA (3×50 ml). The extract was washed with BR (50 ml) dried (Na$_2$SO$_4$) and evaporated to give an oil which was purified by [FCTS] [N] to give a pale yellow oil Trituration with cold ER gave the title compound as a white solid (0.115 g) m.p. 76°–77° mixed m.p. 75.5°–76.5° with the product of Example 2. T.l.c. EN[N] Rf 0.31.

EXAMPLE 11

2,2-Dimethyl-α-[[[6-(4-phenylbutoxy)hexyl](phenylmethyl)amino]methyl]-4H-1,3-benzodioxin-6-methanol A solution of Intermediate 16 (0.24 g) and Intermediate 7 (0.8 g) in dry THF (3 ml) was refluxed under nitrogen for 24 h. The mixture was evaporated and the residue purified by [FCS] [J] to afford the title compound as a pale yellow oil (0.18 g). T.l.c. [O] Rf 0.49.

EXAMPLE 12

2,2-Dimethyl-α-[[[6-(4-phenylbutoxy)hexyl](phenylmethyl)amino]methyl]-4H-1,3-benzodioxin-6-methanol A solution of Intermediate 15 (0.2 g) and Intermediate 7 (0.7 g) in dry THF (5 ml) was refluxed under nitrogen for 18 h. The mixture was diluted with ER (15 ml), washed with 8% NaHCO$_3$ solution (15 ml), BR (10 ml), dried and evaporated to give an oil (0.8 g). Purification by [FCS] (20 g) [J] afforded the title compound as a pale yellow oil (0.09 g). T.l.c. [O] Rf 0.49.

EXAMPLE 13

4-Hydroxy-α$^1$-[[[6-(4-phenylbutoxy)hexyl]amino]methyl]-1,3-benzenedimethanol

A solution of the product of Example 7 (0.3 g) in methanol (2 ml) was diluted with 2M hydrochloric acid (2 ml) and the solution was kept at 23° for 5 h. EA (15 ml) was added and the mixture washed with 8% NaHCO$_3$ (15 ml), BR (15 ml), dried and evaporated in vacuo to give a colourless oil. Trituration with ER afforded the title compound as a white solid (0.23 g) m.p. 76°–77°, mixed m.p. 75.5°–77° with the product of Example 2. T.l.c. EN[N] Rf 0.31.

EXAMPLE 14

4-Hydroxy-α$^1$-[[[6-(4-phenylbutoxy)hexyl]amino]methyl]-1,3-benzenedimethanol

The product described in Example 5 (230 g) in ethanol (1.3 l) was reduced by hydrogen in the presence of 10% palladium-on-carbon catalyst (46.5% paste in H$_2$O; 60 g). Catalyst and solvent were removed and ER (2 l) was added to the residue. The solution was decanted from a little insoluble gum and left to stand overnight. Filtration of the mixture afforded the title compound (147 g), m.p. 75°–77°.

EXAMPLE 15

4-Hydroxy-α$^1$-[[[6-(2-phenylethoxy)hexyl]amino]methyl]-1,3-benzenedimethanol, hydrate A solution of Intermediate 20 (30 mg) in EA (20 ml) was hydrogenated over palladium-charcoal (10%, ~20 mg) for 5 h, filtered through Hyflo and concentrated under reduced pressure to give the title compound as a pal yellow solid (27 mg). T.l.c. (EA-ethanol-NH$_3$ 10:1:1) Rf 0.3. H.p.l.c. Column: 5μ Hypersil 5 mm×10 mm; λmax: 276 nm; Flowrate: 2 ml/min; Eluant: HX-EA-Isopropanol-NH$_3$ 10:1:1:0.15. Retention time 11.5 min.

EXAMPLE 16

4-Hydroxy-α¹-[[[6-(4-phenylbutoxy)hexyl]amino]methyl]-1,3-benzenedimethanol benzoate salt A solution of the compound of Example 2 (2.3 g) in EA (5 ml) at 40° was added to a solution of benzoic acid (0.7 g) in EA (5 ml) at 40°. The solution was cooled to 0° and EA was decanted from the resulting solid. The solid was washed with ER (3×5 ml) and recrystallised from EA to give the title compound as a white solid m.p. 117°–117.5°.

EXAMPLE 17

4-Hydroxy-α¹-[[[6-(4-phenylbutoxy)hexyl]amino]methyl]-1,3-benzenedimethanol 2-hydroxybenzoate (salt).

A solution of 2-hydroxybenzoic acid (0.83 g) in warm isopropanol (10 ml) was added to the compound of Example 2 (2.50 g) in isopropanol (10 ml). The mixture was aged overnight at ambient temperature then the product was collected, washed with isopropanol (3×5 ml) and dried in vacuo at 60°, to give the title salt as a colourless solid, m.p. 134°–135°.

The following salts (Examples 18–21) were prepared in a similar manner from the compound of Example 2.

EXAMPLE 18

4-Hydroxy-α¹-[[[6-(4-phenylbutoxy)hexyl]amino]methyl]-1,3-benzenedimethanol 4-chlorobenzoate (salt)

The product melted at 117°–119°, partially resolidified and remelted at 134°.

EXAMPLE 19

4-hydroxy-α¹-[[[6-(4-phenylbutoxy)hexyl]amino]methyl]-1,3-benzenedimethanol 4-hydroxybenzoate (salt)

M.p. 136.5°–138°.

EXAMPLE 20

4-Hydroxy-α¹-[[[6-(4-phenylbutoxy)hexyl]amino]methyl]-1,3-benzenedimethanol 1-hydroxy-2-naphthalenecarboxylate (salt), M.p. 137°–138°.

EXAMPLE 21

4-Hydroxy-α¹-[[[6-(4-phenylbutoxy)hexyl]amino]methyl]-1,3-benzenedimethanol 3-hydroxy-2-naphthalenecarboxylate (salt)

M.p. 135°–137°.

EXAMPLE 22

4-Hydroxy-α¹-[[[6-(4-phenylbutoxy)hexyl]amino]methyl]-1,3-benzenedimethanol sulphate (2:1) (salt)

Sulphuric acid (98% w/w, 613 mg) was added to ethanol (10 ml) and a portion of the solution (5.2 ml) was added to a warm solution of the base of the compound of Example 2 (2.5 g) in ethanol (10 ml). On being allowed to stand in an open necked flask for 24 h the solution deposited white needles which were filtered off, washed with ethanol (2×5 ml) and dried at 50° in vacuo to give the title salt (1.89 g), m.p. 117.5°–119.5°.

EXAMPLE 23

4-Hydroxy-α¹-[[[6-(3-phenylpropoxy)hexyl]amino]methyl]-1,3-benzenedimethanol

A mixture of Intermediate 1 (0.84 g), Intermediate 21 (1.0 g), N,N-diisopropylethylamine (0.706 g, 0.95 ml) and DMF (7.3 ml) was heated at 80° for 1 h. The clear brown solution was diluted with H₂O (75 ml), acidified to pH4 with 2N hydrochloric acid and then basified to pH8 with solid KHCO₃. The cloudy aqueous phase was extracted with EA (2×75 ml) and the combined extracts were washed successively with H₂O (75 ml) and BR (35 ml). The combined dried (Na₂SO₄) extracts were evaporated and the residual oil was purified by [FCS][I] to give, after trituration with ER (25 ml) the title compound (0.279 g) as a white solid m.p. 77°–78°. T.l.c. [I] Rf 0.13.

EXAMPLE 24

4-Hydroxy-α¹-[[(phenylmethyl)-[6-(3-phenylpropoxy)hexyl]amino]methyl]-1,3-benzenedimethanol Intermediate 23 was added during 15 min to a solution of sodium bis(2-methoxyethoxy)aluminium hydride (3.4M solution in toluene; 33 ml) and CH₂Cl₂ (50 ml), whilst maintaining the temperature between 4° and 18°, under nitrogen. After 1.75 h at 15° the mixture was cooled to 5° and treated very cautiously with H₂O (10 ml). The filtrate was evaporated under reduced pressure and the residue in EA (250 ml) was treated with 2N hydrochloric acid (250 ml). The organic layer was washed successively with 2N Na₂CO₃ solution (200 ml) and H₂O (200 ml), dried and evaporated to give the title compound as an orange oil (15.8 g). T.l.c. (ER) Rf 0.3.

EXAMPLE 25

4-Hydroxy-α¹-[[[6-(3-phenylpropoxy)hexyl]amino]methyl]-1,3-benzenedimethanol

The product of Example 24 (19 g) in ethanol (150 ml) was hydrogenated in the presence of 10% palladium-on-charcoal catalyst (5.2 g). After 2 h 40 min the mixture was filtered and the filtrate evaporated under reduced pressure to a pale yellow oil, which crystallised from EA to give the title compound as a white solid, (10.1 g) m.p. 82°–84°.

Analysis Found: C,71.76;H,8.60;N,3.43. C₂₅H₃₅NO₄ requires C,71.78;H,8.79;N,3.49%.

EXAMPLE 26

4-Hydroxy-α¹-[[(phenylmethyl)-[6-(3-phenylpropoxy)hexyl]amino]methyl]-1,3-benzenedimethanol A solution of 4-bromoacetyl-2-(hydroxymethyl)-phenol diacetate [prepared from 4-acetyl-2-(hydroxymethyl)phenol diacetate (30 g)] in CHCl₃(221 ml) was treated with propylene oxide (16.7 g) and Intermediate 22 hydrochloride (43.4 g). The mixture was stirred and heated at reflux for 24 h, and allowed to cool to RT. Solvent was removed under reduced pressure, the residue was dissolved in toluene (200 ml) and washed with H₂O (2×50 ml). The toluene solution was evaporated to dryness and the residue was dissolved in a mixture of ethanol (270 ml), H₂O (117 ml), and 10N hydrochloric acid (89 ml). The mixture was allowed to stand at RT for 48 h and evaporated to dryness to give an oil. This crude hydrochloride was dissolved in ethanol (283 ml) and the stirred solution was treated with a solution of NaOH (3.53 g) in H₂O (3.53 ml) keeping the temperature below 20°. The solution was cooled to below 10°, and a solution of NaBH₄ (9.15 g) and NaOH (1.26 g) in H₂O (34.9 ml) was added over 0.5 h keeping the temperature below 10°. The mixture was stirred at 20° for 24 h and then adjusted to pH 7.3 with 5N sulphuric acid and evaporated to dryness. The residue was dissolved in a mixture of EA (291 ml) and 2N Na$_2$CO$_3$ (176 ml). The aqueous phase was extracted with EA (2×117 ml), the combined EA solution was washed with 1N Na$_2$CO$_3$ (162 ml) and H$_2$O (8×162 ml) and then evaporated to dryness. The resulting oil was purified by column chromatography (Sorbsil, 500 g) [O] to give the title compound as an oil (17.0 g). This compound was reduced, as described in Example 25, to the compound of Example 23.

EXAMPLE 27

4-Hydroxy-α$^1$-[[[6-(3-phenylpropoxy)hexyl]amino]methyl]-1,3-benzenedimethanol, sulphate (2:1) salt A solution of concentrated sulphuric acid (0.3 g) in ethanol (5 ml) was added to a warm solution of the base of Example 23 (2.4 g) in ethanol (10 ml). The title salt precipitated as a white solid (1.9 g), m.p. 111°–112°.

EXAMPLE 28

4-Hydroxy-α$^1$-[[[6-[4-(2-methoxyphenyl)butoxy]hexyl]amino]methyl]-1,3-benzenedimethanol Intermediate 24 (2.0 g) was added dropwise to a solution of Intermediate 1 (2.13 g), triethylamine (5 ml), and potassium iodide (0.95 g) in DMF (50 ml) at 70°. The solution was heated at 70°–75° for 1 h and added to H$_2$O (800 ml). The resulting emulsion was extracted with EA (3×200 ml) and the dried extract was evaporated to leave an orange oil. The oil was purified on a column of silica (150 ml) [I] to leave a colourless oil. The oil was crystallised from EA to give the title compound as an off-white solid (0.80 g) m.p. 52°–54°. T.l.c. [M] Rf 0.2.

EXAMPLE 29

4-Hydroxy-α$^1$-[[[4-[(6-phenylhexyl)oxy]butyl]amino]methyl]-1,3-benzenedimethanol Intermediate 29 (1.0 g) was added dropwise to a solution of Intermediate 1 (1.2 g) and triethylamine (2 ml) in DMF (30 ml) at 60°. The solution was stirred at 60°–70° for 4 h and added to H$_2$O (500 ml). The resulting emulsion was extracted with EA (3×150 ml) and the dried extract was evaporated to leave a brown oil. The oil was purified on a column of silica (Merck 9385; 150 ml) [I] to leave a yellow gum. The gum was repurified on a column of silica (Merck 9385, 50 ml) eluted with EA-methanol (93:7) to leave a colourless oil. Trituration of the oil with ER (10 ml) gave the title compound as a white solid (0.07 g) m.p. 75°–77°. T.l.c. [M] Rf 0.15.

EXAMPLE 30

α$^1$-[[[6-[2-(2,6-Dimethylphenyl)ethoxy]hexyl]amino]methyl]-4-hydroxy-1,3-benzenedimethanol, hemihydrate Intermediate 30 (2.0 g) was added dropwise to a solution of Intermediate 1 (2.34 g), potassium iodide (0.9 g) and triethylamine (4 g) in DMF (60 ml) at 60°. The solution was stirred at 60°–70° for 1 h and added to H$_2$O (800 ml). The emulsion was evaporated to leave a yellow oil. Purification of the oil on a column of silica (100 ml) [I] gave a colourless oil. Trituration of this oil with ER (25 ml) gave a white solid which was crystallised from EA to give the title compound as a white solid (0.43 g) m.p. 83°–86°. T.l.c. [M] Rf 0.15.

The following Examples were prepared in a similar manner to that described for Example 23 from Intermediate 1 and the other Intermediate shown in the Table.

EXAMPLE 31

4-Hydroxy-α$^1$-[[[6-[4-(4-methoxyphenyl)butoxy]hexyl]amino]methyl]-1,3-benzenedimethanol

EXAMPLE 32

4-Hydroxy-α$^1$-[[[5-[(5-phenylpentyl)oxy]pentyl]amino]methyl]-1,3-benzenedimethanol

EXAMPLE 33

α$^1$-[[[6-[2-(4-Chlorophenyl)ethoxy]hexyl]amino]methyl]-4-hydroxy-1,3-benzenedimethanol

EXAMPLE 34

α$^1$-[[[6-[3-(4-Fluorophenyl)propoxy]hexyl]amino]methyl]-4-hydroxy-1,3-benzenedimethanol

EXAMPLE 35

4-Hydroxy-α$^1$-[[8-[(2-phenylethoxy)octyl]amino]methyl]-1,3-benzenedimethanol

EXAMPLE 36

4-Hydroxy-α$^1$-[[[6-[(5-phenylpentyl)oxy]hexyl]amino]methyl]-1,3-benzenedimethanol

EXAMPLE 37

α$^1$-[[[6-[2-(4-Ethylphenyl)ethoxy]hexyl]amino]methyl]-4-hydroxy-1,3-benzenedimethanol

EXAMPLE 38

4-Hydroxy-α$^1$-[[[7-(3-phenylpropoxy)heptyl]amino]methyl]-1,3-benzenedimethanol

EXAMPLE 39

α$^1$-[[[6-[4-(1,3-Benzodioxol-5-yl)butoxy]hexyl]amino]methyl]-4-hydroxy-1,3-benzenedimethanol

EXAMPLE 40

α$^1$-[[[6-[2-(3-Chlorophenyl)ethoxy]hexyl]amino]methyl]-4-hydroxy-1,3-benzenedimethanol

EXAMPLE 41

4-Hydroxy-α$^1$-[[[6-(phenylmethoxy)hexyl]amino]methyl]-1,3-benzenedimethanol

EXAMPLE 42

α$^1$-[[[6-[3-(2-Fluorophenyl)propoxy]hexyl]amino]methyl]-4-hydroxy-1,3-benzenedimethanol

EXAMPLE 43

4-Hydroxy-α$^1$-[[[(4-phenylbutoxy)butyl]amino]methyl]-1,3-benzenedimethanol

EXAMPLE 44

4-Hydroxy-α$^1$-[[[[4-(5-phenylpentyl)oxy]butyl]amino]methyl]-1,3-benzenedimethanol

EXAMPLE 45

4-Hydroxy-α$^1$-[[7-[(2-phenylethoxy)heptyl]amino]methyl]-1,3-benzenedimethanol

EXAMPLE 46

α$^1$-[[[5-[2-(4-Ethylphenyl)ethoxy]pentyl]amino]methyl]-4-hydroxy-1,3-benzenedimethanol

EXAMPLE 47

4-Hydroxy-α$^1$-[[[6-[2-(4-methylphenyl)ethoxy]hexyl]amino]methyl]-1,3-benzenedimethanol

EXAMPLE 48

4-Hydroxy-α¹-[[[4-(2-phenylethoxy)butyl]amino]methyl]-1,3-benzenedimethanol

EXAMPLE 49

4-Hydroxy-α¹-[[[5-(2-phenylethoxy)pentyl]amino]methyl]-1,3-benzenedimethanol hydrochloride

EXAMPLE 50

4-Hydroxy-α¹-[[[5-(3-phenylpropoxy)pentyl]amino]methyl]-1,3-benzenedimethanol hydrochloride

| Example | Intermediate | Chromatography eluents EA—Methanol—NEt₃ | M.p. °C |
|---|---|---|---|
| 31 | 31 | 90:10:1* | 81–82 |
| 32 | 32 | 85:15:1* | 66–67 |
| 33 | 33 | 89:10:1 | 89–91 |
| 34 | 34 | 89:10:1 | 63–67 |
| 35 | 35 | No chromatography | 97–99 |
| 36 | 36 + KI | 89:10:1 | 75–77 |
| 37 | 37 + KI | 89:10:1 | 96–99 |
| 38 | 38 | 89:10:1 | 72–75 |
| 39 | 39 | 4:1:0* | 68–70 |
| 40 | 40 | 89:10:1 | 76–78 |
| 41 | + | 79:20:1 | 69–70 |
| 42 | 41 | 89:10:1 | 79–81 |
| 43 | 45 | 3:1:0* | 63–68 |
| 44 | 46 | 7:10:1 | 66–71 |
| 45 | 47 | 90:10:1 | 80–81 |
| 46 | 48 | 3:1:0* | 75–78 |
| 47 | 49 | 3:1:0* | 88.5–93.5 |
| 48 | 50 | 4:1:0* | 75–78 |
| 49 | 51 | 3:1* | 66–67 (hydrochloride) |
| 50 | 52 | 3:1* | 50–56 (Hydrochloride) |

*The silica was deactivated with NEt₃
⁺[1-[(6-Bromohexyl)oxy]methyl]benzene

EXAMPLE 51

4-Hydroxy-α¹-[[[5-(4-phenylbutoxy)pentyl]amino]methyl]-1,3-benzenedimethanol

A mixture of Intermediate 1 (1.15 g), DMF (10 ml), N,N-diisopropylethylamine (1.2 g) and Intermediate 53 (0.9 g) was heated at 75° for 2 h. The mixture was diluted with H₂O (150 ml) acidified to pH4 with 2M hydrochloric acid, basified to pH8 with solid KHCO₃ and extracted with EA (2×80 ml). The extracts were washed with H₂O (50 ml) Br (50 ml), dried (Na₂SO₄) and evaporated in vacuo to give an oil which was purified by [FCTS] using EA-methanol-triethylamine (85:15:1) as the eluant to give the product as an oil. This was dissolved in warm (15 ml) and cooled to give the title compound as an off-white solid (0.35 g) m.p. 117°–119°.

T.l.c. EN (EA-CH₃OH 17:3) Rf 0.32.

EXAMPLE 52

4-Hydroxy-α¹-[[[6-[2-(4-methoxyphenyl)ethoxy]hexyl]amino]methyl]-1,3-benzenedimethanol A mixture of Intermediate 1 (0.95 g), Intermediate 54 (1.50 g) and N,N-diisopropylethylamine (1.35 ml) in DMF (molecular sieve dried, 11 ml) was heated at 80° for 1 h under nitrogen. The clear brown solution was basified with 8% NaHCO₃ solution (36 ml) and the cloudy mixture was extracted with EA (3×110 ml). The combined organic extracts were washed consecutively with H₂O (110 ml) and BR (50 ml), dried (Na₂SO₄) and evaporated. The resultant oil (2.43 g) was purified by [FCS] [I] to give a solid which, on trituration with ER (25 ml) gave the title compound as a white solid (0.582 g), m.p. 101°–102°.

Analysis Found: C, 68.65; H, 8.55; N, 3.35. C₂₄H₃₅NO₅ requires C, 69.05; H, 8.45; N, 3.35%.

EXAMPLE 53

4-Hydroxy-α¹-[[[1-methyl-6-(2-phenylethoxy)hexyl]amino]methyl]-1,3-benzenedimethanol A solution of Intermediate 4 (0.94 g) and Intermediate 55 (0.6 g) in ethanol (40 ml) was hydrogenated over 10% palladium on charcoal (0.25 g) and 5% platinum on charcoal (0.25 g) for 20 h, filtered, and evaporated. The residue was purified on a column of silica (Merck 9385, 50 ml) [I] to give a colourless oil. Trituration of the oil with ER (10 ml) gave the title compound as a white solid (0.3 g), m.p. 68°–76°.

T.l.c. [M] Rf 0.2.

EXAMPLE 54

4-Hydroxy-α¹-[[[1-methyl-6-(4-phenylbutoxy)hexyl]amino]methyl]-1,3-benzendimethanol A solution of Intermediate 4 (1.39 g) and Intermediate 56 (1.0 g) in ethanol (40 ml) was hydrogenated over 10% palladium on charcoal (0.2 g) and 5% platinum on charcoal (0.2 g) for 26 h, filtered and evaporated. The residue was purified on a column of silica (Merck 9385; 100 ml) [I] to give the title compound as a white solid (0.62 g) m.p. 57°–60°.

T.l.c. [M] Rf 0.2.

EXAMPLE 55

4-Hydroxy-α¹-[[[1-methyl-5-(3-phenylpropoxy)pentyl]amino]methyl]-1,3-benzenedimethanol A solution of Intermediate 4 (1.6 g) and Intermediate 58 (1.0 g) in ethanol (60 ml) was hydrogenated over 10% palladium on charcoal (0.3 g) and 5% platinum on charcoal (0.3 g) for 20 h, filtered and evaporated. The residue was purified on a column of silica (Merck 9385; 90 ml) [I] to give a colourless oil. Trituration of the oil with ER (20 ml) gave the title compound as a white solid (0.8 g) m.p. 86°–93°.

T.l.c. [M] Rf 0.25.

EXAMPLE 56

4-Hydroxy-α¹-[[[1-ethyl-6-(2-phenylethoxy)hexyl]amino]methy]-1,3-benzenedimethanol A solution of Intermediate 60 (1.0 g) and Intermediate 4 (2.19) in absolute ethanol (60 ml) was hydrogenated over a mixture of palladium on carbon catalyst (200 mg) and platinum on carbon catalyst (200 mg) at RT and atmospheric pressure. After 18 h, the mixture was filtered and the filtrate evaporated in vacuo to give a yellow solid. Purification by [FCTS] (120 g) with EA-methanol-triethylamine (95:5:1) as eluant gave the title compound as a white solid (480 mg) m.p. 82°–84°.

T.l.c. EN (EA-methanol) (19:1) Rf 0.37.

EXAMPLE 57

4-Hydroxy-α¹-[[[1-methyl-5-(4-phenylbutoxy)pentyl]amino]methyl]-1,3-benzenedimethanol A solution of Intermediate 4 (1.45 g) and Intermediate 59 (1.0 g) in ethanol (60 ml) was hydrogenated over 10% palladium on charcoal (0.3 g) and 5% platinum on charcoal (0.3 g) for 20 h, filtered and evaporated. The residue was purified on a column of silica (Merck 9385;

100 ml) [I] to give a colourless oil. Trituration of the oil with ER (20 ml) gave the title compound as a white solid (0.9 g) m.p. 64°-66°.

T.l.c. [M] Rf 0.2.

EXAMPLE 58

4-Hydroxy-$\alpha^1$-[[[5-(2-phenylethoxy)-1-propylpentyl]amino]methyl]-1,3-benzenedimethanol benzoate salt A solution of Intermediate 4 (2.77 g) and Intermediate 61 (2.0 g) in ethanol (120 ml) was hydrogenated over 10% palladium on charcoal (0.25 g) and 5% platinum on charcoal (0.45 g) for 22 h, filtered and evaporated. The residue was purified on a column of silica (Merck 9385; 150 ml) eluted with EA-methanol-triethylamine (19:1:0.1) to give a colourless oil (0.5 g). The oil in CHCl$_3$ (5 ml) was added to benzoic acid (0.2 g) in CHCl$_3$ (5 ml) and the CHCl$_3$ was evaporated. The residue was triturated with ER (3×25 ml) to give the title compound as a white solid (0.36 g) m.p. 67°-69°. T.l.c. [M] Rf 0.35.

EXAMPLE 59

$\alpha^1$-[[[6-[2-(4-Fluorophenyl)ethoxy]-1-methylhexyl]amino]methyl]-4-hydroxy-1,3-benzenedimethanol Intermediate 63 (623 mg) and Intermediate 4 (896 mg) in ethanol (20 ml) were hydrogenated over pre-reduced 5% platinum oxide-on-carbon (0.3 g) and 10%-palladium oxide-on-carbon (50% paste with H$_2$O, 0.35 g) until uptake of hydrogen ceased. The catalyst was removed by filtration (Hyflo) and the residue purified by [FCS] eluting with EA-methanol-triethylamine (94:5:1→89:10:1) to give, after trituration with ER the title compound as a cream solid (652 mg) m.p. 60°-62°.

Analysis Found: C, 68.75; H, 8.45; N, 3.25. C$_{24}$H$_{34}$FNO$_4$ requires C, 68.7; H, 8.15; N, 3.35%.

EXAMPLE 60

4-Hydroxy-$\alpha^1$-[[[6-[3-(4-methoxyphenyl)propoxy]-1-methylhexyl]amino]methyl]-1,3-benzenedimethanol A solution of Intermediate 65 (1.45 g) and Intermediate 1 (0.954 g) in acetic acid (0.311 g) and methanol (22 ml) was treated with sodium cyanoborohydride (0.228 g) at RT. The mixture was stirred for 16 h, and poured into 8% aqueous NaHCO$_3$ (30 ml) and extracted with EA (3×30 ml). The combined dried (Na$_2$SO$_4$) extracts were evaporated to give an oil (1.06 g) which was purified by [FCS] [I]. The resulting oil was triturated with ER (25 ml) and evaporated to give the title compound as a white solid (0.713 g) m.p. 75°-77°. T.l.c. [I] Rf 0.19.

EXAMPLE 61

$\alpha^1$-[[[1,1-Dimethyl-5-(3-phenylpropoxy)pentyl]amino]methyl]-4-hydroxy-1,3-benzenedimethanol A solution of Intermediate 67 (0.70 g) in ethanol (35 ml) was hydrogenated over 5% platinum on charcoal (0.2 g) for 30 min, filtered and evaporated. The residue was triturated with CX-ER 9:1 to give the title compound as a white solid (0.51 g) m.p. 67°-69°.

T.l.c. [M] Rf 0.3.

EXAMPLE 62

$\alpha^1$-[[[1,1-Dimethyl-6-(2-phenylethoxy)hexyl]amino]methyl-4-hydroxy-1,3-benzenedimethanol A solution of methyl 5-(bromoacetyl)-2-hydroxybenzoate (2.2 g) Intermediate 70 (2.0 g) and N,N-diisopropyl ethylamine (1.16 g) in EA (40 ml) was refluxed for 3 h, filtered and evaporated. The residue in ER (50 ml) was filtered and the filtrate added dropwise to a suspension of LiAlH$_4$ (1.6 g) to ER (100 ml) at 0°. The mixture was stirred at RT for 2 h, treated cautiously with H$_2$O (10 ml), acidified to pH1 with hydrochloric acid (2M), and basified to pH8 with solid K$_2$CO$_3$. The resulting slurry was extracted with CHCl$_3$ (4×200 ml) and the dried extract was evaporated. The residue was purified on a column of silica (Merck 9385; 150 ml) to give the title compound as a beige solid (0.3 g) m.p. 68°-71°. T.l.c. [M] Rf 0.2.

EXAMPLE 63

(R)-(−)-4-Hydroxy-$\alpha^1$-[[[6-(3-phenylpropoxy)hexyl]amino]methyl]-1,3-benzenedimethanol Intermediate 77 (750 mg) was hydrogenated in absolute ethanol (60 ml) over pre-reduced 10% palladium oxide on carbon (50% paste, 150 mg). After 2 h, uptake of hydrogen (70 ml) ceased. The catalyst was removed by filtration through Hyflo and the filtrate was concentrated in vacuo. The crude product was purified by [FCS] using EA-methanol-triethylamine 80:20:1 as eluant to give the title compound as a very viscous oil (270 mg).

Specific Rotation T.l.c. (EA-methanol-triethylamine 80:20:1) Rf=0.22.

Analysis Found: C, 71.44; H, 8.34; N, 3.40. C$_{24}$H$_{35}$NO$_4$ requires C, 71.79; H, 8.79; N, 3.49%.

EXAMPLE 64

4-Hydroxy-$\alpha^1$-[[[6-phenylpropoxy)hexyl]amino]methyl]-1,3-benzenedimethanol (a)

1-[4-Hydoxy-3-(hydroxymethyl)phenyl]-2-[6-(3-phenylpropoxy)hexyl](phenylmethyl)amino]ethanone N,N-Diisopropylethylamine (2.77 g) in CH$_2$Cl$_2$ (5 ml) was added to a stirred suspension of 2-bromo-1-[4-hydroxy-3-(hydroxymethyl)phenyl]ethanone (2.5 g) and Intermediate 22 (4.15 g) in CH$_2$Cl$_2$ (30 ml). The solution was kept at 23° for 24 h, washed with H$_2$O (5×17.5 ml) and evaporated in vacuo to give the crude product (a) as an oil. T.l.c. (isopropyl acetate: light petroleum, b.p. 60°-80°, 1:1) Rf 0.4.

(4-Hydroxy-$\alpha^1$-[[[6-(3-phenylpropoxy)hexyl]amino]methyl-1,3-benzenedimethanol A solution of the crude product (a) in absolute ethanol (120 ml) was hydrogenated at 40° and atmospheric pressure over 10% palladium on carbon (0.1 g) and 10% platinum on carbon (0.1 g) catalysts. The mixture was filtered through Hyflo and evaporated to give an oil. The oil was dissolved in EA, the solution evaporated under reduced pressure and the residual oil was triturated with EA (5 ml) to give the title compound as a white solid m.p. 81°-82.5°.

T.l.c. (EA:CH$_3$OH:NH$_3$ 30:10:1) Rf 0.35.

The stimulant action at $\beta_2$-adrenoreceptors of compounds of the invention was determined using the following:

GUINEA-PIG TRACHEAL STRIP PREPARATION

Tracheal rings were mounted in a superfusion apparatus, and continuously superfused with oxygenated physiological (Kreb's) solution containing indomethacin (2.4×10$^{-6}$M) and atropine (4×10$^{-7}$M) at 37° at a rate of 2 ml/min. Changes in tension of the preparation were measured using an isometric strain gauge. Preparation were contracted for the duration of the test by the inclusion of prostaglandin $F_2\alpha$ ($2.9\times 10^{-6}$M) in the superfusion fluid. Two bolus dose-effect curves to the standard, isoprenaline, ($1\times 10^{-12}$–$1\times 10^{-9}$ moles) were obtained at the start of each test in a cumulative fashion, allowing the relaxation obtained with each to reach its own maximum before the next increment was made. On completion of this dose-effect curve, sufficient time was allowed for the tissue to recover (15–30 min). After this time, sequential concentration-effect curves were constructed for first isoprenaline and then the test compound. These were constructed as follows: a low concentration (isoprenaline $3\times 10^{-10}$M; test compound $1\times 10^{-10}$M) was infused until any response obtained had reached its maximum, then the infusion was stopped and the tissue allowed to recover for a maximum of 30 min. After this period the procedure was repeated using progressively increasing concentrations of agonist, and in this way, whole concentration-effect curves obtained. Potency was determined by comparison of the concentration-effect curve thus constructed with that previously obtained for isoprenaline and expressed as equipotent concentration (isoprenaline =1) i.e.

$$\frac{EC_{50} \text{ test compound}}{EC_{50} \text{ isoprenaline}}$$

was calculated.

Duration of action was also measured for each response, and is the time taken from stopping the infusion to 50% recovery. Graphs were drawn for duration times against response magnitude, and from these, duration times for 50% maximum responses were determined.

The ability of compounds of the invention to afford protection against histamine-induced bronchoconstriction was demonstrated using the following:

CONSCIOUS GUINEA PIG TEST

The principle of the method is that bronchoconstriction leads to a decrease in tidal volume, and hence to an increase in respiratory rate. Guinea pigs were placed in a whole body plesythmograph, i.e. a chamber separated, by means of a collar, into 2 parts—a head chamber and a body chamber. Pressure changes in the body chamber were monitored by means of a low pressure transducer, from which was derived a continuous, linear recording of respiratory rate by means of an instantaneous ratemeter connected to a chart recorded. The head chamber was connected to an expansion chamber into which a histamine aerosol was driven from a solution of set concentration (usually 5 mg/ml) for a predetermined period (usually 10–15 seconds). At the end of this period, the aerosol was switched off, but the guinea pig was left in contact with the aerosolized histamine still in the expansion chamber until his respiratory rate increased by 40%, or for a total of 4 min, whichever was the sooner. The degree of bronchoconstriction was expressed in terms of the area under the respiratory rate curve. Guinea-pig were challenged at intervals until their rate responses were constant, then they were given a dose of the test compound by either aerosol or oral route, and the response to histamine reassessed first at 30 min post dose, and then at intervals thereafter for up to 24 h post dose. By testing a range of doses of the test compound, a dose-relationship in the maximum protection was determined, and the time taken (up to 24 h) for the response to histamine challenge to return to pre-test compound protection levels determined. Each dose of each test compound was tested in at least 4 animals.

PHARMACEUTICAL EXAMPLES

Tablets

These may be prepared by the normal methods such as wet granulation or direct compression.

| A. Direct Compression | |
|---|---|
| | mg/tablet |
| Active ingredient | 2.0 |
| Microcrystalline Cellulose USP | 196.5 |
| Magnesium Stearate BP | 1.5 |
| Compression weight | 200.0 |

The active ingredient is sieved through a suitable sieve, blended with the excipients and compressed using 7 mm diameter punches.

Tablets of other strengths may be prepared by altering the ratio of active ingredient to microcrystalline cellulose or the compression weight and using punches to suit.

| B. Wet Granulation | |
|---|---|
| | mg/tablet |
| Active ingredient | 2.0 |
| Lactose BP | 151.5 |
| Starch BP | 30.0 |
| Pregelatinised Maize Starch BP | 15.0 |
| Magnesium Stearate BP | 1.5 |
| Compression weight | 200.0 |

The active ingredient is seived through a suitable sieve and blended with lactose, starch and pregelatinised maize starch. Suitable volumes of purified water are added and the powders are granulated. After drying, the granules are screened and blended with the magnesium stearate. The granules are then compressed into tablets using 7 mm diameter punches.

Tablets of other strengths may be prepared by altering the ratio of active ingredient to lactose or the compression weight and using punches to suit.

| C. For buccal administration | |
|---|---|
| | mg/tablet |
| Active ingredient | 2.0 |
| Lactose BP | 94.8 |
| Sucrose BP | 86.7 |
| Hydroxypropylmethylcellulose | 15.0 |
| Magnesium Stearate BP | 1.5 |
| Compression weight | 200.0 |

The active ingredient is sieved through a suitable sieve and blended with the lactose, sucrose and hydroxypropylmethylcellulose. Suitable volumes of purified water are added and the powders are granulated. After drying, the granules are screened and blended with the magnesium stearate. The granules are then compressed into tablets using suitable punches.

The tablets may be film coated with suitable film forming materials, such as hydroxypropyl methylcellulose, using standard techniques. Alternatively the tablets may be sugar coated.

Capsules

|  | mg/capsule |
|---|---|
| Active ingredient | 2.0 |
| *Starch 1500 | 97.0 |
| Magnesium Stearate BP | 1.0 |
| Fill Weight | 100.0 |

*A form of directly compressible starch.

The active ingredient is sieved and blended with the excipients. The mix is filled into size No. 2 hard gelatin capsules using suitable machinery. Other doses may be prepared by altering the fill weight and if necessary changing the capsule size to suit.

Syrup

This may be either a surcose or sucrose free presentation.

A. Sucrose Syrup

|  | mg/5 ml dose |
|---|---|
| Active ingredient | 2.0 |
| Sucrose BP | 2750.0 |
| Glycerine BP | 500.0 |
| Buffer | |
| Flavour | |
| Colour | as required |
| Preservative | |
| Purified Water BP to | 5.0 ml |

The active ingredient, buffer, flavour, colour and preservative are dissolved in some of the water and the glycerine is added. The remainder of the water is heated to dissolve the sucrose and is then cooled. The two solutions are combined, adjusted to volume and mixed. The syrup produced is clarified by filtration.

B. Sucrose-Free

|  | mg/5 ml dose |
|---|---|
| Active ingredient | 2.0 mg |
| Hydroxypropyl methylcellulose USP (viscosity type 4000) | 22.5 mg |
| Buffer | |
| Flavour | |
| Colour | |
| Preservative | as required |
| Sweetener | |
| Purified Water BP to | 5.0 ml |

The hydroxypropyl methylcellulose is dispersed in hot water, cooled and then mixed with an aqueous solution containing the active ingredient and the other components of the formulation. The resultant solution is adjusted to volume and mixed. The syrup produced is clarified by filtration.

Suppositories

| Active ingredient | 2.0 mg |
|---|---|
| *Witepsol H15 to | 1.0 g |

*A proprietary grade of Adeps Solidus Ph. Eur.

A suspension of the active ingredient in molten Witepsol is prepared and filled, using suitable machinery, into 1 g size suppository moulds.

Injection for Intravenous Administration

|  | mg/ml |
|---|---|
| Active ingredient | 0.5 mg |
| Sodium Chloride BP | as required |
| Water for Injection BP to | 1.0 ml |

Sodium chloride may be added to adjust the tonicity of the solution and the pH may be adjusted, using acid or alkali, to that of optimum stability and/or facilitate solution of the active ingredient. Alternatively suitable buffer salts may be used.

The solution is prepared, clarified and filled into appropriate size ampoules sealed by fusion of the glass. The injection is sterilised by heating in an autoclave using one of the acceptable cycles. Alternatively the solution may be sterilised by filtration and filled into sterile ampoules under aseptic conditions. The solution may be packed under an inert atmosphere of nitrogen or other suitable gas.

Inhalation Cartridges

|  | mg/cartridge |
|---|---|
| Active ingredient micronised | 0.200 |
| Lacrose BP to | 25.0 |

The active ingredient is micronised in a fluid energy mill to a fine particle size range prior to blending with normal tabletting grade lactose in a high energy mixer. The powder blend is filled into No. 3 hard gelatin capsules on a suitable encapsulating machine. The contents of the cartridges are administered using a powder inhaler such as the Glaxo Rotahaler.

Metered Dose Pressurised Aerosol

A. Suspension Aerosol

|  | mg/metered dose | Per can |
|---|---|---|
| Active ingredient micronised | 0.100 | 26.40 mg |
| Oleic Acid BP | 0.010 | 2.64 mg |
| Trichlorofluoromethane BP | 23.64 | 5.67 g |
| Dichlorodifluoromethane BP | 61.25 | 14.70 g |

The active ingredient is micronised in a fluid energy mill to a fine particle size range. The Oleic Acid is mixed with the Trichlorofluoromethane at a temperature of 10°–15° C. and the micronised drug is mixed into the solution with a high shear mixer. The suspension is metered into aluminium aerosol cans and suitable metering valves, delivering 85 mg of suspension are crimped onto the cans and the Dichlorodifluoromethane is pressure filled into the cans through the valves.

B. Solution Aerosol

|  | mg/metered dose | Per can |
|---|---|---|
| Active ingredient | 0.100 | 24.0 mg |
| Ethanol BP | 7.500 | 1.80 g |
| Trichlorofluoromethane BP | 18.875 | 4.53 g |
| Dichlorodifluoromethane BP | 48.525 | 11.65 g |

Oleic acid BP, or a suitable surfactant e.g. Span 85 (sorbitan trioleate) may also be included.

The active ingredient is dissolved in the ethanol together with the oleic acid or surfactant if used. The alcoholic solution is metered into suitable aerosol containers followed by the trichlorofluoromethane. Suitable metering valves are crimped onto the containers and dichlorodifluoromethane is pressure filled into them through the valves.

'Active Ingredient' is used in the above examples to represent a compound of the invention, and can be, for example, the compound of Example 2.

We claim:

1. 4-Hydroxy-alpha'-[[[6-(4-phenylbutoxy)hexyl]amino]methyl]-1,3-benzenedimethanol,1-hydroxy-2-naphthalenecarboxylate.

2. 4-Hydroxy-alpha'-[[[6-(4-phenylbutoxy)hexyl]amino]methyl]-1,3-benzenedimethanol and its physiologically acceptable salts and solvates.

3. A pharmaceutical composition comprising the compound of claim 1 together with one or more physiologically acceptable carriers or excipients.

4. A pharmaceutical composition comprising at least one of the compounds of claim 2, together with one or more physiologically acceptable carriers or excipients.

5. 4-Hydroxy-alpha'-[[[6-(3-phenylpropoxy)hexyl]amino]methyl]1,3-benzenedimethanol and its physiologically acceptable salts and solvates.

6. A pharmaceutical composition comprising at least one of the compounds of claim 5, together with one or more physiologically acceptable carriers or excipients.

7. A method of treating a patient suffering from a disease associated with reversible airways obstruction which comprises administering to the patient an effective amount of the compound of claim 1.

8. A method of treating a patient suffering from a disease associated with reversible airways obstruction which comprises administering to the patient an effective amount of at least one of the compounds of claim 2.

9. A method of treating a patient suffering from a disease associated with reversible airways obstruction which comprises administering to the patient an effective amount of at least one of the compounds of claim 5.

10. A method according to claim 7, wherein the disease is asthma or chronic bronchitis.

11. A method according to claim 8, wherein the disease is asthma or chronic bronchitis.

12. A method according to claim 9, wherein the disease is asthma or chronic bronchitis.

* * * * *